United States Patent
Wands et al.

(10) Patent No.: US 6,770,797 B2
(45) Date of Patent: Aug. 3, 2004

(54) NON-TRANSGENIC NONHUMAN MODEL FOR ALZHEIMER'S DISEASE USING A AD7C-NTP NUCLEIC ACID

(75) Inventors: Jack R. Wands, Waban, MA (US); Suzanne M. de la Monte, East Greenwich, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 09/872,968

(22) Filed: Jun. 1, 2001

(65) Prior Publication Data

US 2003/0050262 A1 Mar. 13, 2003

(51) Int. Cl.$^7$ ................... G01N 33/00; A01K 67/027
(52) U.S. Cl. ................... 800/12; 800/3; 800/14; 800/18
(58) Field of Search ................... 800/3, 12, 14, 800/18

(56) References Cited

U.S. PATENT DOCUMENTS

| | | | |
|---|---|---|---|
| 5,800,390 A | 9/1998 | Hayakawa et al. | 604/93 |
| 5,863,898 A | 1/1999 | Goli et al. | 514/12 |
| 5,948,634 A | 9/1999 | De la Monte et al. | 435/69.1 |
| 6,071,075 A | 6/2000 | Tomita et al. | 416/97 |
| 6,180,784 B1 | 1/2001 | Wolff et al. | 540/474 |

FOREIGN PATENT DOCUMENTS

| | | |
|---|---|---|
| WO | WO 9423756 | 10/1994 |
| WO | WO 96/15272 | 5/1996 |
| WO | WO 98/38204 | 9/1998 |

OTHER PUBLICATIONS

Nishimura et al. (1998) Degeneration in vivo of Rat Hippocampal Neurons by Wild–Type Alzheimer Amyloid Precursor Protein Overexpressed by Adenovirus–Mediated Gene Transfer. Journal of Neuroscience. vol. 18, No. 7, pp. 2387–2398.*

Games et al. (1992) Lack of Alzheimer Pathology After Beta–Amyloid Protein Injections in Rat Brain. Neurobiology of Aging. vol. 13, pp. 569–576.*

Podlisny et al. (1992) Synthetic Amyloid Beta–Protein Fails to Produce Specific Neurotoxicity in Monkey Cerebral Cortex. Neurobiology of Aging. vol. 13, pp. 561–567.*

Kahle, et al., "Combined Assessment of Tau and Neuronal Thread Protein in Alzheimer's Disease CSF", *Neurology*, 54:1498–1504 (2000).

Kōiv, et al., "Evidence for Ternary Complex Formation by Histone HI, DNA, and Liposomes", *Biochemistry*, 34:8018–8027 (1995).

Zelphati, et al., "Mechanism of Oligonucleotide Release from Cationic Liposomes", *Proc. Natl. Acad. Sci. USA*, 93:11493–11498 (1996).

Zhao, et al., "Alternative Pulmonary Defense in Transgenic Mice Deficient in NOS Isozymes by Gene–Knockout Technique", Abstract, *FASEB Journal*, 3(5):A1015 (1999).

Czubayko et al., "Ribozyme–Elucidates a Direct Role of Pleiotrophin in Tumor Growth," 1994, J. Biol. Chem. 269:21358–21363.

de la Monte et al., "Microtiter Immunocytochemical ELISA Assay", 1999, Biotechniques 26:1073–1976.

de la Monte et al., "Characterization of the AD7C–NTP cDNA Expression in Alzheimer's Disease and Measurement of a 41–kD Protein in Cerebrospinal Fluid," 1997, J. Clin. Invest. 100(12):30393–3104.

de la Monte et al., "Aberrant expression of nitric oxide synthase III in Alzheimer's disease: relevance to cerebral vasculopathy and neurodegeneration," Neurobiol. Aging, Mar.–Apr. 2000; 21(2):309–319.

GENBANK™ Accession No. NM014486.

GENBANK™ Accession No. AF010144.

Kobayashi et al., "Reversal of Drug Sensitivity in Multi–Resistant Tumor Cells by an MDR 1 ( PGY 1) Ribozyme," 1994, Cancer Res. 54:1271–1275.

Mahieu et al, "Construction of a Ribozyme Directed Against Human Interleukin–6 mRNA: Evaluation of Its Catalytic Activity In Vitro and In Vivo," 1994, Blood 84:3758–65.

Melani et al., "Inhibition of Proliferation by c–myb Antisense Oligodeozynucleotides in Colon Adenocarcinoma Cell Lines That Express c–myb," Cancer Res. 51:2897–2901, 1991.

Quon et al, Formation of β–Amyloid Protein Deposits in Brains of Transgenic Mice. Nature, Jul. 18, 1991, vol. 352, pp. 239–241.

Sullivan et al., "Development of Ribozymes for Gene Therapy," 1994, J. Invest. Derm. 103:85S–89S.

\* cited by examiner

*Primary Examiner*—Deborah Crouch
(74) *Attorney, Agent, or Firm*—Ingrid A. Beattie; Mintz, Levin, Cohn, Ferris, Glovsky and Popeo, P.C.

(57) ABSTRACT

The invention features a non-transgenic model of Alzheimer's Disease, method for inducing prolonged in vivo gene expression in a mammal, and methods of inhibiting Alzheimer's Disease-associated neuronal cell death.

12 Claims, 18 Drawing Sheets

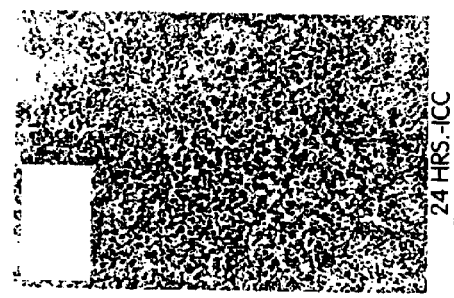
Fig. 7A 24 HRS.-ICC pAD7c-NTP
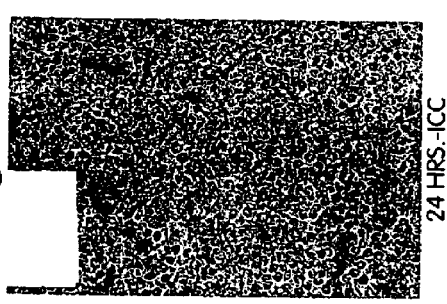
Fig. 7D 24 HRS.-ICC pLuc
Fig. 7B 72 HRS.-ICC pAD7c-NTP
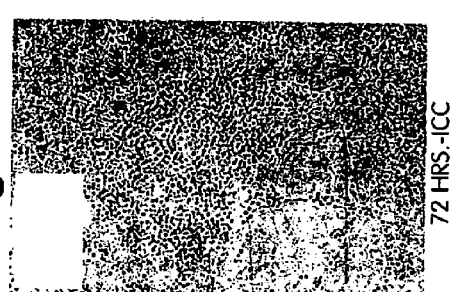
Fig. 7E 72 HRS.-ICC pLuc
Fig. 7C 72 HRS.-PHASE pAD7c-NTP
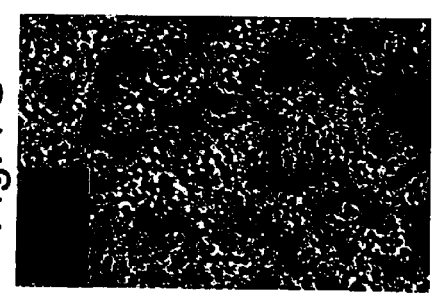
Fig. 7F 72 HRS.-PHASE pLuc

 
Fig. 14A　　　　　　　　　Fig. 14B
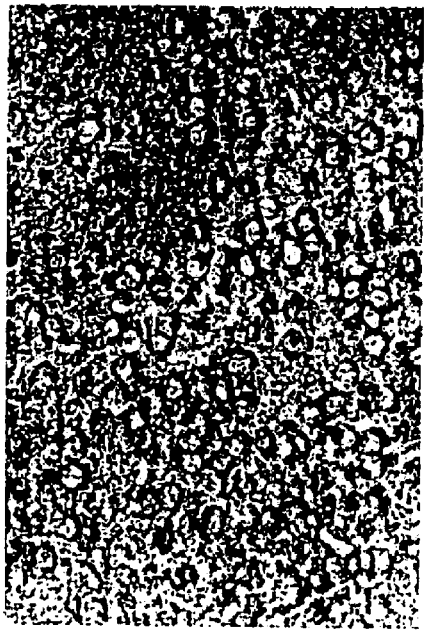 
Fig. 14C　　　　　　　　　Fig. 14D

SEQUENCE LISTING

<160> NUMBER OF SEQ ID NOS: 2

<210> SEQ ID NO 1
<211> LENGTH: 1442
<212> TYPE: DNA
<213> ORGANISM: Homo sapiens

<400> SEQUENCE: 1

```
tttttttttt tgagatggag ttttcgctct tgttgcccag gctggagtgc aatggcgcaa      60
tctcagctca ccgcaacctc cgcctcccgg gttcaagcga ttctcctgcc tcagcctccc     120
cagtagctgg gattacaggc atgtgcaccc acgctcggct aatttttgtat ttttttttag    180
tagagatgga gtttctccat gttggtcagg ctggtctcga actcccgacc tcagatgatc     240
cctccgtctc ggcctcccaa agtgctagat acaggactgg ccaccatgcc cggctctgcc    300
tggctaattt ttgtggtaga acagggttt cactgatgtg cccaagctgg tctcctgagc      360
tcaagcagtc cacctgcctc agcctcccaa agtgctggga ttacaggcgt gcagccgtgc    420
ctggcctttt tattttatttt tttttaagac acaggtgtcc cactcttacc caggatgaag    480
tgcagtggtg tgatcacagc tcactgcagc cttcaactcc tgagatcaag catcctcctg    540
cctcagcctc ccaagtagct gggaccaaag acatgcacca ctacacctgg ctaattttta    600
tttttatttt taatttttttg agacagagtc tcaactctgt cacccaggct ggagtgcagt    660
ggcgcaatct tggctcactg caacctctgc ctcccgggtt caagttattc tcctgcccca    720
gcctcctgag tagctgggac tacaggcgcc caccacgcct agctaatttt tttgtatttt    780
tagtagagat gggggttcacc atgttcgcca ggttgatctt gatctctgga ccttgtgatc    840
tgcctgcctc ggcctcccaa agtgctggga ttacaggcgt gagccaccac gcccggctta    900
tttttaattt ttgtttgttt gaaatggaat ctcactctgt tacccaggct ggagtgcaat    960
ggccaaatct cggctcactg caacctctgc ctcccgggct caagcgattc tcctgtctca   1020
gcctcccaag cagctgggat tacgggcacc tgccaccaca ccccgctaat ttttgtattt   1080
tcattagagg cggggtttca ccatatttgt caggctggtc tcaaactcct gacctcaggt   1140
gacccacctg cctcagcctt ccaaagtgct gggattacag gcgtgagcca cctcacccag   1200
ccggctaatt tagataaaaa aatatgtagc aatgggggt cttgctatgt tgcccaggct   1260
ggtctcaaac ttctggcttc atgcaatcct tccaaatgag ccacaacacc cagccagtca   1320
catttttttaa acagttacat ctttatttta gtatactaga aagtaataca ataaacatgt   1380
caaacctgca aattcagtag taacagagtt cttttataac ttttaaacaa agctttagag   1440
ca                                                                   1442
```

<210> SEQ ID NO 2
<211> LENGTH: 375

```
<212> TYPE: PRT
<213> ORGANISM: Homo sapiens

<400> SEQUENCE: 2

Met Glu Phe Ser Leu Leu Leu Pro Arg Leu Glu Cys Asn Gly Ala Ile
  1               5                  10                  15

Ser Ala His Arg Asn Leu Arg Leu Pro Gly Ser Ser Asp Ser Pro Ala
             20                  25                  30

Ser Ala Ser Pro Val Ala Gly Ile Thr Gly Met Cys Thr His Ala Arg
         35                  40                  45

Leu Ile Leu Tyr Phe Phe Leu Val Glu Met Glu Phe Leu His Val Gly
     50                  55                  60

Gln Ala Gly Leu Glu Leu Pro Thr Ser Asp Asp Pro Ser Val Ser Ala
 65                  70                  75                  80

Ser Gln Ser Ala Arg Tyr Arg Thr Gly His His Ala Arg Leu Cys Leu
                 85                  90                  95

Ala Asn Phe Cys Gly Arg Asn Arg Val Ser Leu Met Cys Pro Ser Trp
            100                 105                 110

Ser Pro Glu Leu Lys Gln Ser Thr Cys Leu Ser Leu Pro Lys Cys Trp
            115                 120                 125

Asp Tyr Arg Arg Ala Ala Val Pro Gly Leu Phe Ile Leu Phe Phe Leu
        130                 135                 140

Arg His Arg Cys Pro Thr Leu Thr Gln Asp Glu Val Gln Trp Cys Asp
145                 150                 155                 160

His Ser Ser Leu Gln Pro Ser Thr Pro Glu Ile Lys His Pro Pro Ala
                165                 170                 175

Ser Ala Ser Gln Val Ala Gly Thr Lys Asp Met His His Tyr Thr Trp
            180                 185                 190

Leu Ile Phe Ile Phe Ile Phe Asn Phe Leu Arg Gln Ser Leu Asn Ser
        195                 200                 205

Val Thr Gln Ala Gly Val Gln Trp Arg Asn Leu Gly Ser Leu Gln Pro
    210                 215                 220

Leu Pro Pro Gly Phe Lys Leu Phe Ser Cys Pro Ser Leu Leu Ser Ser
225                 230                 235                 240

Trp Asp Tyr Arg Arg Pro Pro Arg Leu Ala Asn Phe Val Phe Leu
                245                 250                 255

Val Glu Met Gly Phe Thr Met Phe Ala Arg Leu Ile Leu Ile Ser Gly
            260                 265                 270

Pro Cys Asp Leu Pro Ala Ser Ala Ser Gln Ser Ala Gly Ile Thr Gly
        275                 280                 285

Val Ser His His Ala Arg Leu Ile Phe Asn Phe Cys Leu Phe Glu Met
    290                 295                 300

Glu Ser His Ser Val Thr Gln Ala Gly Val Gln Trp Pro Asn Leu Gly
305                 310                 315                 320

Ser Leu Gln Pro Leu Pro Pro Gly Leu Lys Arg Phe Ser Cys Leu Ser
                325                 330                 335

Leu Pro Ser Ser Trp Asp Tyr Gly His Leu Pro Pro His Pro Ala Asn
            340                 345                 350

Phe Cys Ile Phe Ile Arg Gly Gly Val Ser Pro Tyr Leu Ser Gly Trp
        355                 360                 365

Ser Gln Thr Pro Asp Leu Arg
370                 375
```

NON-TRANSGENIC NONHUMAN MODEL FOR ALZHEIMER'S DISEASE USING A AD7C-NTP NUCLEIC ACID

STATEMENT AS TO FEDERALLY SPONSORED RESEARCH

This invention was made with U.S. government support under National Institutes of Health grant number AA-02666 and AA-10102. The government has certain rights in the invention.

BACKGROUND OF THE INVENTION

This invention relates to neurodegenerative conditions.

Alzheimer's Disease is a neurodegenerative illness characterized by memory loss and other cognitive deficits. The prevalence of Alzheimer's Disease increases with age, and the presence of the disease is difficult to determine without brain biopsy. Alzheimer's Disease is characterized by the presence of neuritic plaques, neurofibrillary tangles, and neuronal cell death. Post-mortem slices of brain tissue from Alzheimer's disease patients exhibit the presence of amyloid in the form of proteinaceous extracellular cores of the neuritic plaques. The amyloid cores of these neuritic plaques are composed of a protein called the amyloid-beta or amyloid-b. Amyloid-containing neuritic plaques are a prominent feature of selective areas of the brain in Alzheimer's Disease patients as well as patients afflicted with Downs Syndrome. However, little is known about the development of Alzheimer's Disease or the mechanisms, which contribute to the disease.

SUMMARY OF THE INVENTION

The invention features a non-transgenic animal model for Alzheimer's Disease and methods for inducing prolonged in vivo gene expression in the brain. Prolonged expression of an exogenous nucleic acid in a mammal is achieved by contacting a cells or tissue with a composition, which contains a nucleic acid, a histone, and an amphipathic compound. Preferably, the composition also contains a liposome. The tissue is not skeletal muscle tissue. Preferably, the tissue is neuronal tissue such as central nervous system (CNS) tissue. For example, the tissue contains a post-mitotic neuronal cell, a cortical neuronal cell, a cerebellar neuronal cell, a glial cell, a vascular endothelial cell, or a hippocampal neuronal cell.

Gene expression in the tissue is detected in vivo for at least 48 hours after contacting the tissue with the nucleic acid composition. Preferably, gene expression persists for at least 72 hours, more preferably for at least 96 hours, more preferably for at least one week, and even more preferably for at least two to four weeks after contacting the tissue with the composition. By expression is meant transcription of a nucleic acid molecule. Gene expression is measured by detecting nucleic acid transcripts, or by detecting a translation product. The gene delivery system described herein has been successfully used to achieve gene expression in a target tissue for at least two months (and longer) after contacting the tissue with the composition.

The nucleic acid composition is in the form of a liposome, e.g., a neutral, anionic, or cationic liposome. The composition contains histone proteins, e.g., H1, H2A, H2B, H3, or H4. The amphipathic compound is cationic. For example, the compound is a polyamine, such as, a non-natural polyamine having a hydrophobic moiety such as a C6–C24 alkane, C6–C24 alkene, sterol, steroid, lipid, fatty acid, or a hydrophobic hormone. Optionally, the composition contains a nuclear localizing signal.

The nucleic acid portion of the composition is any polypeptide-encoding DNA or antisense template. To induce Alzheimer Disease physiological conditions in vivo, the nucleic acid encodes an Alzheimer's Disease-associated neural thread protein (AD-NTP) such as Alzheimer's Disease-associated neural thread protein 7c (AD7c-NTP)

An antisense template is one that is transcribed into a nucleic acid molecule that has a sequence that is complementary to a specific mRNA. The transcribed nucleic acid molecule binds to the complementary sequence in the specific mRNA and inhibits translation of the mRNA. An antisense oligonucleotide has a sequence that is complementary to a specific mRNA and binds to the complementary sequence in the specific mRNA to inhibit translation of the mRNA. For example, the nucleic acid portion of the composition is AD7c-NTP antisense molecule or a nitric oxide synthase III (NOS-3) antisense molecule. An AD7c-NTP antisense template is transcribed into an RNA molecule, which binds to a portion of an endogenous AD7c-NTP mRNA in a target cell or tissue and inhibits translation of the AD7c-NTP mRNA into a AD7c-NTP polypeptide or gene product. Similarly, NOS-3 antisense template is transcribed into an RNA molecule, which binds to a portion of an endogenous NOS-3 mRNA in a target cell or tissue and inhibits translation of the NOS-3 mRNA into a NOS-3 polypeptide or gene product. Preferably, the antisense DNA contains a sequence, which is complementary to a DNA sequence in the AD7c-NTP or NOS-3 cDNA sequence. For example, the DNA is complementary to a 5' untranslated region of the gene The composition and method are useful for gene therapy applications or to produce non-human animal model of a human disease state. For example, the nucleic acid portion of the composition contains a sequence encoding a polypeptide such as a AD7c-NTP polypeptide for development of an animal model of Alzheimer's Disease.

The methods are useful to make a non-transgenic model for Alzheimer's Disease. The model is a non-human animal, which contains an exogenous AD7c-NTP nucleic acid in its brain tissue, e.g., in a neuronal cell, of the animal. AD7c-NTP gene product is over-expressed in brain tissues of the animal. The animal model of human Alzheimer's Disease recapitulates the neurodegenerative process and neuropathological changes which occur in the brains of human patients with Alzheimer's Disease. Utilizing the prolonged gene expression system described above, the animal expresses an exogenous AD7c-NTP polypeptide in a neuronal cell of the animal for at least 48 hours and up to and exceeding a period of 4 weeks. Expression has been detected in vivo for up to two months after contacting brain tissue with the exogenous nucleic acid. The animal is a rodent or a non-human primate. Cortical and/or hippocampal neuronal cells express the AD7c-NTP polypeptide over extended periods of time and exhibit physical conditions and symptoms, which mimic human Alzheimer's Disease, e.g., sporadic Alzheimer's Disease. Such conditions include neuritic plaque formation, neuronal cell death by apoptosis (as well as activation of pro-apoptosis genes), and increased levels of phospho-tau, APP and amyloid-b.

Alternatively, the model is a non-human animal, which contains an exogenous nitric oxide synthase nucleic acid, e.g., NOS-3, and which expresses an exogenous nitric oxide synthase polypeptide in a neuronal cell of the animal for at least 48 hours and longer. The physical condition and symptoms of the animal mimic those of human Alzheimer's Disease.

Also within the invention is a method of inhibiting Alzheimer's Disease-associated neuronal cell death, by contacting an AD7c-NTP-overexpressing cell with a composition, which contains an AD7c-NTP antisense nucleic acid (e.g., an antisense template or an antisense ologinucleotide). The composition also contains a histone polypeptide. Optionally, the composition contains an amphipathic compound described above. The AD7c-NTP antisense template (e.g., a DNA) is transcribed into an RNA molecule, which binds to a portion of an endogenous AD7c-NTP mRNA in the overexpressing cell and inhibits translation of the AD7c-NTP gene product. In this manner, AD7c-NTP protein production is regulated and the adverse effects of overproduction reduced. The method is useful as a genetic therapeutic tool to reduce the pathologic symptoms of Alzheimer's Disease, e.g., sporadic Alzheimer's Disease. For example, downregulating pathological overproduction of endogenous AD7c-NTP in this manner leads to decreased production of NOS-3, decreased neuronal cell death, decreased production of amyloid precursor protein (APP) and amyloid-b, as well as decreased formation of neuritic plaques. NOS-3 expression is directly reduced by administering a NOS-3 antisense oligonucleotide or a NOS-3 antisense template.

Alzheimer's Disease associated neuronal cell death is also inhibited by contacting an AD7c-NTP overexpressing neuronal cell with an AD7c-NTP or an NOS-3-specific ribozyme. A ribozyme is an RNA molecule, which contains a catalytic center. For example, the ribozyme is an enzyme, a self-splicing RNA, or a self-cleaving RNA. Ribozymes decrease production of a target protein by inhibiting the translation of the mRNA that encodes the target protein, e.g., AD7c-NTP.

Another method of inhibiting Alzheimer's Disease-associated neuronal cell death involves contacting an AD7c-NTP-overexpressing cell with a compound such as small organic molecule, a peptide, an antibody (or fragment thereof) that inhibits signal transduction via the insulin receptor substrate (IRS) pathway.

Alzheimer's Disease-associated neuronal cell death is inhibited by contacting an AD7c-NTP-overexpressing cell with an inhibitor of an IRS-dependent growth factor. For example, the inhibitor decreases the transcription of an IGF-1 gene, translation of an IGF-1 mRNA, or function of its gene product. In one example, the inhibitor binds to an N-terminal insulin/IGF1 receptor domain in AD7c-NTP, thereby inhibiting binding of endogenous insulin and/or IGF-1 to neuronal cell surface AD7c-NTP. A soluble fragment of AD7c-NTP is used to inhibit IGF-1 binding to cellular AD7c-NTP. For example, the fragment contains the amino acid sequence of residues 2–14 of SEQ ID NO:2. Preferably, the polypeptide fragment is less than 250 residues, less than 200 residues, less than 150 residues, less than 100 residues. For example, the fragment is greater than 13 residues or more, but less than 50 residues, contains the amino acid sequence of residues 2–14 of SEQ ID NO:2, and inhibits signal transduction via the IRS signal transduction pathway. Alternatively, the compound is a drug (e.g., a small organic molecule), peptide, antibody, or an antibody fragment, which binds to the insulin/IGF-1 hybrid domain of AD7c-NTP.

A fragment of a reference protein is a polypeptide, which is shorter in length than the reference protein. The fragment includes a sequence, e.g., at least 10 amino acids, which is identical to the reference protein. The fragment may be 50%, 60%, 75%, 80%, 90%, 95%, and up to 99% of the length of the reference protein. Similarly, a gene fragment is shorter in length than the gene sequence to which it refers but includes a DNA sequence, e.g., at least 18 nucleotides, which is identical to the reference sequence.

Other methods of inhibiting Alzheimer's Disease-associated neuronal cell death, include those which include the step of contacting an AD7c-NTP-overexpressing cell with an inhibitor of nitric oxide synthase III and those which include the step of contacting an AD7c-NTP-overexpressing cell with an inhibitor of insulin.

The invention also features methods of screening for compounds which inhibit the onset or progression of Alzheimer's Disease or inhibit a symptom or physiological condition of the disease methods. Screening assays are carried out in vitro using AD7c-NTP or NOS-3 over-expressing cells. In vivo assays are carried out using the non-transgenic model of AD7c-NTP or NOS-3 overexpression. For example, a method of identifying a compound which inhibits Alzheimer's Disease-associated neuronal cell death is carried out by contacting an AD7c-NTP over-expressing cell with a candidate compound and measuring cell viability. An increase in cell viability in the presence of the compound compared to in its absence indicates that the compound inhibits Alzheimer's Disease associated neuronal cell death. The cell is a primary or immortalized cell line. Preferably the cell is a primary cerebellar neuronal cell, hippocampal cell, glial cell, or vascular endothelial cells which contains an exogenous AD7c-NTP encoding DNA and expresses the exogenous AD7c-NTP polypeptide in an inducible or constitutive manner. Another screening method is carried out by contacting a non-human animal comprising an AD7c-NTP over-expressing cell in a neuronal tissue in vivo, with a candidate compound and measuring neuronal cell viability. An increase in cell viability in the presence of the compound compared to in its absence indicates that the compound inhibits Alzheimer's Disease associated neuronal cell death.

Compounds are screened for the ability to inhibit one or more symptom or physiological characteristic of Alzheimer's Disease. For example, a non-human animal containing an AD7c-NTP over-expressing cell in a neuronal tissue, e.g., the brain, is contacted with a candidate compound. The non-human animal is a transgenic or non-transgenic animal, which has been engineered to overexpress AD7c-NTP or NOS-3 (compared to levels expressed in its wildtype counterparts). The compound is administered systemically or locally. For example, the compound is delivered directly to brain tissue, e.g., by intraventricular infusion. Amyloid precursor protein (APP) expression is detected in the tissue, and a decrease in APP expression in the presence of the compound compared to in its absence indicates that the compound inhibits a symptom of Alzheimer's Disease. Similarly, an assay to identify a compound which inhibits a symptom of Alzheimer's Disease is carried out by contacting a non-human animal comprising an AD7c-NTP over-expressing neuronal cell with a candidate compound and detecting neuritic amyloid plaques in the tissue. A decrease in the amount of plaques in the presence of the compound compared to in its absence indicates that the compound inhibits a symptom of Alzheimer's Disease or decreases the severity of Alzheimer's Disease. The methods allow high throughput screening of candidate compounds to identify therapeutic agents which reduce a pathological condition associated with Alzheimer's Disease.

Other features, objects, and advantages of the invention will be apparent from the description and and from the claims.

BRIEF DESCRIPTION OF THE DRAWINGS

FIGS. 7A–F photographs of neuronal cells showing reduced viability and increased AD7c-NTP expression in postmitotic rat cerebellar neuron cultures transfected with the AD7c-NTP cDNA (FIGS. 7A, C, E) relative to the LacZ control transfected cultures (FIGS. 7B, D, F). FIGS. 7A, B depict phase contrast images of the cultures 72 hours after transfection. Note the conspicuous cell loss and prominent long thin cell processes on most of the remaining granule neurons (arrows). The large flat cells in the background are glial in origin. Parallel cultures were immunostained using the N3I4 monoclonal antibody. Immunoreactivity was detected by the avidin-biotin horseradish peroxidase complex (FIGS. 7A,B,C) method using diaminobenzidine as the chromogen (brown precipitate). Note the abundant AD7c-NTP immunoreactivity present 48 and 72 hours after transfection with the AD7c-NTP cDNA (FIGS. 7C, E), relative to cells transfected with the LacZ control gene (FIGS. 7D, F).

FIGS. 10B and D represent similar regions of rat brains inoculated with the Luciferase control gene. Tissue sections were examined 1 week after gene transfer into the right lateral ventricle and cerebral hemisphere. TUNEL labeling of nuclei reflects increased genomic DNA nicking and fragmentation as occur prior to apoptosis.

FIG. 11C represents a negative control rat brain inoculated with the Luciferase gene. Tissue sections were examined 1 week after gene transfer into the right lateral ventricle and cerebral hemisphere. Increased AD7c-NTP-induced p53 expression was seen in cortical neurons (FIGS. 11A, B) compared with control cerebral cortical neurons (FIG. 11C).

FIG. 12C represents a negative control rat brain inoculated with the Luciferase gene. Tissue sections were examined 1 week after gene transfer into the right lateral ventricle and cerebral hemisphere. Increased AD7c-NTP-induced Bax expression was seen in cortical neurons (FIGS. 12A, B) compared with control cerebral cortical neurons (FIG. 12C).

FIG. 13F represents a negative control rat brain inoculated with the Luciferase gene. Tissue sections were examined 2 weeks after gene transfer into the right lateral ventricle and cerebral hemisphere. Increased NTP immunoreactivity was seen in cortical (FIGS. 13A–C; arrow) and hippocampal (FIG. 13D; arrows) neurons and neuritic plaques (FIG. 13E; arrow) in brains that over-express AD7c-NTP compared with negative control cortical (FIG. 13F) neurons.

FIGS. 14A–D are photographs of neuronal tissue showing aberrant synaptophysin expression in rat brains after AD7c-NTP gene transfer (FIGS. 14A, C). FIGS. 14B and D represent similar regions of rat brains inoculated with the Luciferase control gene. Tissue sections were examined 1 week after gene transfer into the right lateral ventricle and cerebral hemisphere. FIGS. 14A and B show reduced synaptophysin labeling of neuropil fibers with labeling primarily distributed close to the perikarya, possibly reflecting neurite retraction. FIGS. 14C and D show abundant synaptophysin immunoreactivity in cortical neuropil fibers, particularly in Layer I of the cortex (FIG. 14B, outer band of brown labeling)

FIG. 15B represents rat cerebral tissue inoculated with the Luciferase control gene. Tissue sections were examined 2 weeks after gene transfer into the right lateral ventricle and cerebral hemisphere. FIG. 15A shows abnormally increased pTau immunoreactivity in neuronal nuclei. Labeling of cells was absent in a similar region of a control brain (FIG. 15B). The brains inoculated with the AD7c-NTP cDNA also exhibited pTau-immunoreactive neuritic plaques as shown in FIGS. 15C–E.

FIG. 16D represents a negative control rat brain inoculated with the Luciferase gene. Tissue sections were examined 2 weeks after gene transfer into the right lateral ventricle and cerebral hemisphere. Increased APP immunoreactivity was seen in cortical neurons (FIGS. 16A–C) compared with control cerebral cortex (FIG. 16F). Intense APP immunoreactivity was seen in hippocampal neurons (FIG. 16C, double-headed arrows) and in dense core (FIG. 16C, arrow) or neuritic (FIG. 16D, E; arrows) plaque-like structures FIGS. 17B and D represent similar regions of rat brains inoculated with the Luciferase control gene. Tissue sections were examined 2 weeks after gene transfer into the right lateral ventricle and cerebral hemisphere. FIG. 17A shows amyloid-beta in the walls of small intracerebral vessels and cells. FIG. 17C shows dense cores of amyloid beta resembling senile plaques that occur in human brains with Alzheimer's Disease.

FIGS. 18E and F represent negative control rat brains inoculated with the Luciferase gene. Tissue sections were examined 2 weeks after gene transfer into the right lateral ventricle and cerebral hemisphere. Increased NOS-3 immunoreactivity was seen in cortical (FIGS. 18A, B, D) and hippocampal (FIG. 18C) neurons in brains that over-express AD7c-NTP compared with the levels of NOS-3 in control cortical (FIG. 18E) and hippocampal (FIG. 18F) neurons.

DETAILED DESCRIPTION

Figure 1A:
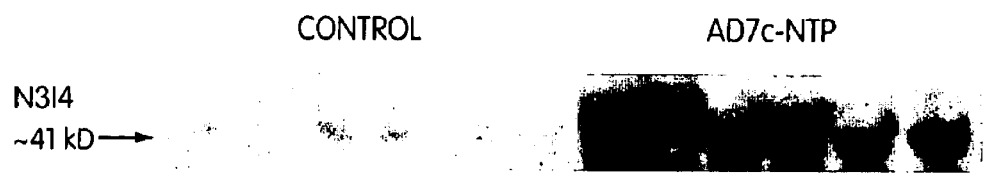
FIG. 1A is a photograph of the results of a Western Blot assay in which IPTG induction of AD7c-NTP expression was measured.

Prior to the invention, consistent, long term heterologous gene expression in neuronal brain tissue had not been achieved. A heterologous nucleic acid or polypeptide, is one that is present in an organism or location, which differs from the organism or location from which it was originally isolated. For example, a heterologous polypeptide is one encoded by a nucleic acid that has been introduced to a cell using the gene delivery methods described herein. Unlike previous gene delivery methods, the gene therapy approach described herein leads to long term expression of therapeutic nucleic acids in adult brain tissue. Prior to the invention, many approaches to gene therapy were unsuccessful because the nucleic acid formulations failed to deliver the gene to the target tissue, failed to achieve high enough levels of expression, or failed to achieve expression for long enough periods of time. The nucleic acid compositions, which contain a nucleic acid, a histone and an amphipathic compound, effectively deliver nucleic acids to neuronal tissue and lead to expression of the gene product for long periods of time.

Prolonged Expression of Therapeutic Nucleic Acids in Adult Neural Tissue

The data described in the examples below were generated in an Alzheimer's Disease model system. The data indicate that any desired gene sequence (e.g., polypeptide-encoding sequence or antisense sequences) is expressed in brain tissue for extended periods of time, e.g., even up to several months post-delivery. The compositions are delivered directly into brain tissue or indirectly, e.g., intravenously. The amphipathic nature of the compositions allow traversal of the blood brain barrier and access to neural tissue. Thus, therapeutic polypeptides, e.g., morphogens, growth factors such as nerve growth factor (NGF) or platelet-derived growth factor (PDGF), and angiogenesis inhibitors, are administered to adult neural tissue to achieve long term clinical benefit. In addition to Alzheimer's Disease, prolonged gene expression as demonstrated herein allows treatment of adult neurological disorders such as age-related neurodegeneration, Parkinson's Disease, ischemic stroke, Huntington's Disease, and brain tumors.

AD7c-NTP Expression in Adult Brain Tissue

AD7c-NTP is expressed at abnormally high levels in brains with Alzheimer's Disease (compared to normal brain tissue) beginning early in the course of neurodegeneration. The protein accumulates in cortical neurons and co-localizes with phospho-tau-immunoreactive cytoskeletal lesions that correlate with dementia.

AD7c-NTP cDNA encodes a ~41 kD membrane-spanning protein that has a hydrophobic leader sequence, a myristoylation site, and potential cleavage site. The protein is expressed on the cell surface or it may be secreted. Increased levels of AD7c-NTP protein are detectable in both cerebrospinal fluid and urine of patients with early or intermediate stages of AD. Over-expression of the AD7c-NTP gene in neuronal cells in vitro produces a dimorphic phenotype characterized by either increased cell death, or neuritic sprouting in the remaining viable cells. AD7c-NTP-induced neuronal cell death is mediated by apoptosis and impaired mitochondrial function and is associated with increased cellular levels of p53 and phospho-tau in AD.

Non-Transgenic Model of Alzheimer's Disease

Prolonged expression of an AD7c-NTP or NOS-3 polypeptide in brain tissue of an animal, e.g., a rodent, leads to a physiological state which resembles human Alzheimer's Disease. Prolonged expression is achieved by administering a nucleic acid encoding AD7c-NTP or NOS-3 in a liposomal mixture with a histone protein and/or an amphipathic compound. Although similar mixtures have been used to induce expression of nucleic acids in skeletal muscle tissue, the prolonged expression described herein has not been achieved in neuronal tissue. Long term expression of exogenous nucleic acids in neuronal tissue was surprising. The model has several advantages over transgenic models of the disease. For example, the nucleic acids are expressed in the brain and not in other tissues, and the expression can be regulated. The target nucleic acid, e.g., AD7c-NTP or NOS-3, is cloned under the regulation of an inducible promoter or a constitutive promoter, which preferentially directs expression of the gene product in brain tissue.

The model is clinically relevant in that a number of clinical indices of Alzheimer's Disease are reflected in an animal, which has been manipulated to express or over-express AD7c-NTP or NOS-3. For example, like Alzheimer's Disease brains, increased expression of phospho-tau, APP, and amyloid-b as well as plaque formation, was evident in the brains of model animals.

Inhibiting Binding to Insulin/IGF-1 Hybrid Domain of AD7c-NTP

Small molecules, polypeptides, antibodies, or antibody fragments which bind to the insulin/IGF-1 domain of AD7c-NTP are used to block or inhibit signal tranduction via the IRS pathway, which in turn, inhibits neuronal cell death. The inhibitory molecules block or reduce signal transduction by inhibiting binding of an endogenous ligand to the insulin/IGF-1 domain of AD7c-NTP.

Antibodies, which bind to AD7c-NTP, have been generated using standard methods. At least 13 different hybridomas, which produce AD7c-NTP-specific antibodies, were identified. To determine whether such antibodies bind to the insulin/IGF-1 domain of AD7c-NTP, a standard binding assay is carried out using an AD7c-NTP peptide containing residues 2–14 of SEQ ID NO:2. For example, a peptide of at least 15 residues containing the insulin/IGF-1 domain of AD7c-NTP is immobilized on a solid matrix. Detectably-labelled antibody (or fragments) are allowed to bind. The antibody or antibody fragments are directly or indirectly labelled, e.g., using a radioactive, fluorescent, or colorimetric label. Unbound antibody is washed away. Retention of the labeled antibody on the solid matrix indicates that the antibody binds to the target domain.

To determine whether an antibody inhibits binding of insulin or IGF-1 to the insulin/IGF-1 domain of AD7c-NTP, a standard competitive binding assay is carried out. For example, a peptide containing the domain is immobilized. The immobilized peptide is incubated with labeled insulin or IGF-1 in the presence and absence of an antibody. A decrease in binding of insulin or IGF-1 to the immobilized peptide in the presence of the antibody (compared to the level of binding in its absence) indicates that the antibody inhibits binding of insulin or IGF-1 to the insulin/IGF-1 domain of AD7c-NTP. Blocking antibodies inhibit signal transduction, and thus, AD7c-NTP-induced neuronal death.

Antibodies, which bind to the insulin/IGF-1 domain of AD7c-NTP are obtained using techniques well known in the art. For example, an antibody is raised by immunizing animals with a polypeptide containing the amino acid sequence of residues 2–14 of SEQ ID NO:2. Antibodies which bind to the domain are generated using methods known in the art, e.g., those described in U.S. Pat. No. 5,863,898. Such antibodies bind to the domain and inhibit insulin or IGF-1 binding, and therefore, signal transduction via the IRS pathway.

Following identification of a hybridoma producing a suitable monoclonal antibody, DNA encoding the antibody is cloned. The cloned DNA may be used to express antibody fragments. The antibody preferably binds to a site in the insulin/IGF-1 domain of AD7c-NTP. The antibody binds to an epitope that is exposed on the surface of the cell. The antibody is a polyclonal antisera or monoclonal antibody. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

For administration to human patients, antibodies, e.g., AD7c-NTP monoclonal antibodies, are humanized by methods known in the art. Antibodies with a desired binding specificity can be commercially humanized (Scotgene, Scotland; Oxford Molecular, Palo Alto, Calif.).

Therapeutic Administration

The compositions described herein are administered to patients diagnosed with Alzheimer's Disease as well as those who are at risk of developing Alzheimer's Disease, e.g., a person with a family history of the disease or who has been identified as having a risk factor for the disease. For example, the compositions are administered prophylactically to an elderly population (e.g., those over the age of 65, 70, or 75 years of age) without evidence of clinical Alzheimer's Disease. The composition is employed to ameliorate or prevent a decline in brain function associated with amyloid formation, that is less severe than dementia. Prophylactic therapy is applied to persons of any age who, while displaying normal brain function, are identified as being at risk for developing Alzheimer's Disease.

The blood-brain barrier may be compromised in patients with neurological disease, e.g., Alzheimer's Disease, allowing systemically administered drugs to pass through the barrier into the CNS. Liposome formulations of therapeutic compounds may also facilitate passage across the blood-brain barrier. Thus, the formulations described herein may be administered systemically. For example, administration is accomplished intravenously, intraarterially, or intrathecally (via the spinal fluid).

Alternatively, the compositions are administered locally, e.g., intraventricularly. Devices for administration of compositions to an internal part of the brain are known in the art, e.g., U.S. Pat. No. 5,800,390. For example, sustained release, solid preparations and semi-solid preparations are administered directly to brain tissue. Administration is carried out by inserting the needle-like member of an intracerebral device which is optionally implanted in the head so that a distal end of the guide is positioned at a site of administration.

An effective amount of a compound is preferably from about 0.1 mg/kg to about 150 mg/kg. The compositions are administered using methods known in the art. For gene therapy or antisense applications, a nucleic acid encoding a therapeutic polypeptide (e.g., NGF or PDGF) or a nucleic acid encoding an antisense compound (e.g., an AD7c-NTP or NOS-3 antisense template) is linked in-frame to a promoter which preferentially directs expression of the sequence to which it is linked in brain tissue. For example, the nucleic acid of interest is linked to a myelin basic protein (MBP) promoter, an APP promoter, a glutamine synthetase promoter, or a tyrosine hydroxylase promoter for enhanced expression of the target nucleic acid sequence in brain tissue.

Antisense therapy is carried out by administering to an animal, e.g., a human patient, antisense template which is transcribed into an antisense RNA. For example, the antisense template is transcribed into a AD7c-NTP or NOS-3 antisense RNA. The antisense RNA binds to endogenous AD7c-NTP or NOS-3 transcripts and inhibits translation of the RNA into an AD7c-NTP gene product. The antisense RNA may be a short (generally at least 10, preferably at least 14 nucleotides, and up to 100 or more nucleotides) nucleotide sequence formulated to be complementary to all or a portion of a specific mRNA sequence. The antisense template is preferably located downstream from the promoter sequences of the gene. A poly A tail is typically located at the end of the antisense sequence to signal the end of the sequence. Standard methods relating to antisense technology have been described (Melani et al., Cancer Res. 51:2897–2901, 1991). Following transcription of the DNA sequence into antisense RNA, the antisense RNA binds to its target mRNA molecules within a cell, thereby inhibiting translation of the mRNA and down-regulating expression of the protein encoded by the mRNA.

For gene therapy or antisense therapy, the claimed DNA is introduced into target cells of an animal, e.g., a patient, using standard vectors. The gene delivery systems include a histone and an amphipathic compound. Suitable gene delivery systems may include liposomes, receptor-mediated delivery systems, naked DNA, and viral vectors such as herpes viruses, retroviruses, adenoviruses, and adenoassociated viruses. Methods for transfecting cells with isolated DNA are well known to those skilled in the art of molecular biology.

DNA are administered in a pharmaceutically acceptable carrier. Pharmaceutically acceptable carriers are biologically compatible vehicles which are suitable for administration to an animal, e.g., physiological saline. A therapeutically effective amount is an amount of DNA which is capable of producing a medically desirable result in a treated animal. As is well known in the medical arts, dosages for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{22}$ copies of the DNA molecule. The compositions of the invention are administered locally or systemically. Administration will generally be intraventricularly or intravenously. The preferred form of the composition to be administered depends on the intended mode of administration and therapeutic application. For example, DNA may be administered in solution form through a catheter port directly into brain tissue.

Ribozyme therapy is also be used to inhibit AD7c-NTP or NOS-3 gene expression in cancer patients. Ribozymes bind to specific mRNA and then cut it at a predetermined cleavage point, thereby destroying the transcript. These RNA molecules are used to inhibit expression of the target gene according to methods known in the art (Sullivan et al., 1994, J. Invest. Derm. 103:85S-89S; Czubayko et al., 1994, J. Biol. Chem. 269:21358–21363; Mahieu et al, 1994, Blood 84:3758–65; Kobayashi et al. 1994, Cancer Res. 54:1271–1275).

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site are evaluated for predicted structural features such as secondary structure that may render the oligonucleotide sequence unsuitable. The suitability of candidate targets are evaluated by testing their accessibility to hybridization with complementary oligonucleotides, using ribonuclease protection assays. Antisense RNA and DNA molecules and ribozymes are prepared by methods known in the art, such as chemically synthesis of oligodeoxyribonucleotides using solid phase phosphoramidite techniques.

Identification of Compounds which Inhibit Conditions Associated with Alzheimer's Disease Assays to identify a compound which inhibits Alzheimer's Disease-associated neuronal cell death are carried out by culturing an AD7c-NTP over-expressing cell with a candidate compound and measuring cell viability. Cell viability is measured using methods known in the art, e.g., vital dye exclusion or incorporation of tritiated thymidine. An increase in cell viability in the presence of the compound compared to in its absence indicates that the compound inhibits Alzheimer's Disease associated neuronal cell death. The cell is a primary or immortalized cell line. Primary cerebellar neuronal cell, hippocampal cell, glial cell, or vascular endothelial cells which over-express AD7c-NTP encoding DNA or NOS-3 encoding DNA in an inducible or constitutive manner are used in the assay. For example, the cells are in the form of neuronal tissue explants from an Alzheimer's Disease patient or Alzheimer's Disease model animal. A non-human animal model for the disease, such as the model described herein in which AD7c-NTP is overexpressed, is contacted with a candidate compound and neuronal cell viability measured. An increase in cell viability in the presence of the compound compared to in its absence indicates that the compound inhibits Alzheimer's Disease associated neuronal cell death.

Other symptoms or conditions of the disease are monitored using the animal model, and compounds are screened for the ability to inhibit one or more symptom or physiological conditions of Alzheimer's Disease. Candidate compounds such as organic compounds, polypeptides, or antibodies and fragments thereof, are administered systemically or directly to brain tissue of the animal. APP expression is detected in the tissue using known methods such as immunohistochemical analysis. A decrease in APP expression in the presence of the compound compared to in its absence indicates that the compound inhibits a symptom or condition of Alzheimer's Disease.

The animal model of Alzheimer's Disease described herein develops senile neuritic plaques similar to those detected in autopsy samples of human brains from Alzheimer's Disease patients. Compounds which inhibit the formation or progression of plaques are identified by contacting the non-human animal model with a candidate compound and detecting amyloid plaques in the tissue. Plaques are detected using known methods such as histological and immunohistological evaluation of brain tissue and vascular tissue in the brain. A decrease in the amount of plaques in the presence of the compound compared to in its absence indicates that the compound inhibits senile plaque formation.

Compounds which bind to the insulin/IGF-1 domain of AD7c-NTP (residues 2–14 of SEQ ID NO:2) block binding of insulin or IGF-1 to AD7c-NTP and inhibit signal transduction. Such compounds are identified using standard methods. For example, candidate polypeptides, antibodies, or other compounds are immobilized, e.g, on a chromatographic column or on another solid matrix such as a microarray or microtiter plate. The immobilized compounds are contacted with detectably-labelled polypeptide (e.g., a polypeptide containing residues 2–14 of SEQ ID NO:2). Unbound peptide is washed away, and the label is detected.

Compositions which bind to the insulin/IGF-1 domain of AD7c-NTP are identified by retention of the detectably-labeled AD7c-NTP polypeptide.

Alternatively, a competitive binding assay is carried out. A polypeptide containing residues 2–14 of SEQ ID NO:2 is immobilized and contacted with insulin or IGF-1 in the presence and absence of a candidate compound. For example, the candidate compound is an AD7c-NTP antibody or an antibody fragment of an AD7c-NTP-specific antibody. The insulin or IGF-1 may be detectably labelled. A decrease in binding of insulin or IGF-1 to the immobilized AD7c-NTP peptide (as detected by presence of label) in the presence of the candidate compound compared to the level of binding in the absence of the compound indicates that the candidate compound inhibits binding of insulin or IGF-1 to the insulin/IGF-1 hybrid domain of AD7c-NTP. Such inhibitory compounds inhibit signal transduction via the insulin/IGF-1 signal transduction pathway, and thus, inhibit a symptom or condition of Alzheimer's Disease.

AD7c-NTP-induced neuronal cell death associated with Alzheimer's Disease is mediated by apoptosis. Apoptotic death is associated with increased cellular levels of p53 and phospho-tau, as occur in AD. Accordingly, another method of screening for therapeutic agents is carried out by contacting AD7c-NTP over-expressing cells (or NOS-3 over-expressing cells) with a candidate compound in vitro or in vivo and measuring the level of p53 and phospho-tau in the cells. A decrease in the level of p53 or phospho-tau in the presence of the candidate compound compared to the level in the absence of the candidate compound indicates that the candidate compound reduces neuronal cell death associated with Alzheimer's Disease.

EXAMPLE 1
AD7c-NTP Induced Apoptosis and Sprouting

The AD7c-NTP neuronal thread protein gene is over-expressed in Alzheimer's disease beginning early in the course of disease. AD7c-NTP protein accumulates in cortical neurons and co-localizes with phospho-tau-immunoreactive cytoskeletal lesions. Over-expression of the AD7c-NTP gene results in a dimorphic phenotype associated with both apoptosis and enhanced neuritic sprouting. An inducible mammalian expression vector was used to regulate AD7c-NTP expression in PNET2 neuronal cells, and the effects of insulin (50 nM), IGF-1 (5 ng/ml), NGF (2.5 ng/ml) or PDGF (5 ng/ml) stimulation on cellular morphology, gene expression, and intracellular signaling pertinent to AD-type neurodegeneration was examined. Cells transfected with the CAT gene were used as negative controls. Insulin or IGF-1 stimulation of cells induced to express AD7c-NTP resulted in increased cell death, increased levels of p53, p21/Waf1, phospho-JNK, nitric oxide synthase-3, phospho-tau, and the p25 regulatory partner of Cdk 5, and inhibition of Bcl2 expression. In contrast, cells stimulated with NGF or PDGF, despite high levels of AD7c-NTP expression, exhibited prominent neuritic sprouting, and high levels of Bcl-2 and phospho-Erk MAPK. These results indicate that the apoptosis and sprouting phenotypes associated with AD7c-NTP over-expression are regulated by the availability and cellular responses to different growth factors. These data indicate that neuronal cells that over-express AD7c-NTP were rescued by NGF or PDGF stimulation.

Establishment of an Inducible Expression System to Study AD7c-NTP Over-expression in Vitro.

Prior to the invention, cells stably transfected with AD7c-NTP could not be maintained because of progressive cell death. Therefore, an inducible system of AD7c-NTP expression was established using the LacSwitch II mammalian expression vector (Stratagene, La Jolla, Calif.). PNET2 human CNS neuronal cells were stably transfected with the pCMVLacII vector in which the Lac repressor protein driven by a CMV promoter. The Lac repressor protein is targeted to the nucleus by the nuclear localization sequence. Stable clones were selected with hygromycin B. Clones were transfected with a second vector (pOPRSV1) carrying the AD7c-NTP cDNA or the chloramphenicol acetyltransferase (CAT) gene, and stable clones were selected with hygromycin and G418. The second vector contains an RSV promoter that drives expression of the gene of interest, and an ideal operator sequences for Lac repressor binding. Isopropyl-1-□-D-thiogalactopyranoside (IPTG) stimulation (1–5 mM) turns off the Lac repressor protein and induces expression of CAT or AD7c-NTP within 4–8 hours. After induction, gene expression persists for 48–96 hours, and is rapidly inhibited by withdrawal of IPTG. Exploratory studies demonstrated that 3 mM IPTG was optimum for inducing gene expression in the clones.

Growth Factor Stimulation

To examine the effects of different growth factors on AD7c-NTP expression (and over-expression), the cells were serum-starved for 16 hours, after which IPTG (1–5 mM) was added to the medium. Four hours later, the cells were stimulated with insulin (50 nM), IGF-1 (5 ng/ml), NGF (5 ng/ml), or platelet-derived growth factor (PDGF; 5 ng/ml) for 24–72 hours. The cells were analyzed for morphological changes, viability, AD7c-NTP immunoreactivity, and expression of pro-apoptosis genes, survival genes, and phospho-tau.

Viability Assay

Viability was measured by a standard crystal violet assay. Crystal violet dye labels only viable cells. The assays were performed with cells seeded into 96-well plates at a density of $2\times10^4$ cells/well. The absorbances were measured using a Spectracount plate reader (Packard, Meriden, Conn.). The crystal violet absorbances increased linearly with cell density between $10^4$ and $5\times10^5$ cells/well.

Protein Expression

Standard Western blot assays wew used to measure cellular levels of p53, Bcl-2, p21/Waf1, phospho-tau, tau, c-fos, NTP, and activated (phosphorylated) forms of Erk mitogen activated protein (MAP) kinase, amino-terminal c-jun-activated kinase (pJNK), and p38/HOG1. Immunoprecipitation followed by Western blot analysis was used to measure p85 subunit associated with IRS1. For Western blot analysis of p53 Bcl-2, phospho-tau, tau, c-fos, and NTP, the cells were lysed in ice cold radioimmunoprecipitation assay (RIPA) buffer supplemented with protease and phosphatase inhibitors. For the immunoprecipitation studies, Western blot analysis of phospho-Erk, pJNK, and p38, and the PI3 kinase assays, the cells were harvested in Triton lysis buffer supplemented with protease and phosphatase inhibitors. Protein concentrations were measured using the BCA assay (Pierce, Rockford, Ill.). Samples containing 60 µg of protein were fractionated by sodium dodecyl sulfate polyacrylamide gel electrophoresis (SDS-PAGE), then transferred to PVDF membranes, and analyzed by Western immunoblotting. Immunoreactivity was detected with horseradish peroxidase conjugated secondary IgG and PicoWest enhanced chemiluminescence reagents (Pierce Chemical Company, Rockford, Ill.). CAT activity was measured using known methods.

Microtiter Immunocytochemical ELISA (MICE) Assay

The MICE assay is known in the art (e.g., as described by de la Monte et al., 1999, Biotechniques 26:107301076). The assay is a rapid and sensitive method for quantifying immunoreactivity in 96-well micro-cultures and combines the advantages of the enzyme-linked immunosorbant assay with immunocytochemical staining to permit sensitive in situ quantification of protein expression with values normalized to cell density. The cells were fixed in Histochoice (Amresco, Solon, Ohio), permeabilized with 0.05% saponin in Tris-buffered saline (50 mM Tris, pH 7.5, 0.9% NaCl; TBS), and blocked with Superblock-TBS (Pierce, Rockford, Ill.). The cells were then incubated overnight at 4° C. with primary antibody diluted in TBST-BSA. Immunoreactivity was detected using horseradish peroxidase conjugated secondary antibody (Pierce, Rockford, Ill.) and the TMB soluble peroxidase substrate (Pierce, Rockford, Ill.). Absorbances were measured at 450 nm using a Spectracount plate reader.

To compare the levels of protein expression it was necessary to correct for differences in cell density. After measuring immunoreactivity, the plates were washed in TBS and the cells were stained 0.1% Coomassie blue dye in 40% methanol/10% acetic acid. After extensively washing the plates in water, the dye was eluted with 1% SDS in PBS (200 $\mu$l/well). The absorbances (560 nm) were measured using a Spectracount plate reader (Packard Instrument Company, Meriden, Conn.). The MICE index was calculated from the ratio of the absorbances measured for immunoreactivity and cell density. Coomassie blue absorbance increases linearly with cell density between $1\times10^4$ and $5\times10^5$ cells per well. Eight or 16 replicate culture wells were analyzed in each experiment. All experiments were repeated at least 3 times.

Measurement of Phosphatidylinositol-3 Kinase (PI3K) Activity

The cells were harvested in Triton lysis buffer supplemented with protease and phosphatase inhibitors. Total PI3K was immunoprecipitated from 500 $\mu$g protein in cell lysates using rabbit polyclonal antibodies to the p85 subunit of PI3K and Protein A sepharose. The immunoprecipitants were incubated for 5 minutes at room temperature with 10 $\mu$g of sonicated phosphatidylinositol in HEPES buffer (200 mM HEPES, 4 mM EGTA, 4 mM sodium phosphate, pH 7.0). Reactions were initiated by the addition of 5 $\mu$Ci [$\alpha^{32}$P] ATP, 15 mM MgCl$_2$, 150 mM ATP, 1.5 mM Tris-HCl, pH 7.4, and 15 mM NaCl. After 10 minutes incubation at 30° C., the reactions were stopped by the addition of HCl to a final concentration of 1.2 N, followed by chloroform/methanol extraction. Phosphorylated lipids were analyzed by thin layer chromatography using gel plates pre-coated with 1% oxalate (Merck, White House Station, N.J.). PI3K activity was measured with a phosphorimager.

Antibodies and Chemicals

Monoclonal antibodies to p53 and p21/Waf1, and polyclonal antibodies to c-fos were obtained from Oncogene Research Products (Cambridge, Mass.). Rabbit polyclonal antibody to the insulin receptor substrate −1 and the p85 subunit of PI3K was purchased from Upstate Biotechnology, Inc. (Lake Placid, N.Y.). Polyclonal antibody to Bcl-2 was purchased from Santa Cruz Biotechnology (Santa Cruz, Calif.), and antibodies to both total and activated JNK, Erk MAPK, and p38/HOG1 were obtained from Promega Corp. (Madison, Wis.). Anti-tau was purchased from Dako Corp. (Carpenteria, Calif.). Protein A sepharose was purchased from Amersham-Pharmacia Biotechnology (Arlington Heights, Ill.). Recombinant human NGF, PDGF, and IGFI were purchased from Sigma Co (St. Louis, Mo.). Human insulin was purchased from Novagen.

Statistical Analysis

Data described in this example represent the means±S.D.'s generated with results obtained from 3 to 6 experiments. Inter-group comparisons were made using Student t-tests or analysis of variance (ANOVA) with Fisher least significant difference (LSD) post-hoc tests.

AD7c-NTP Over-expression in Transfected PNET2 Neuronal Cells

Figure 1B:
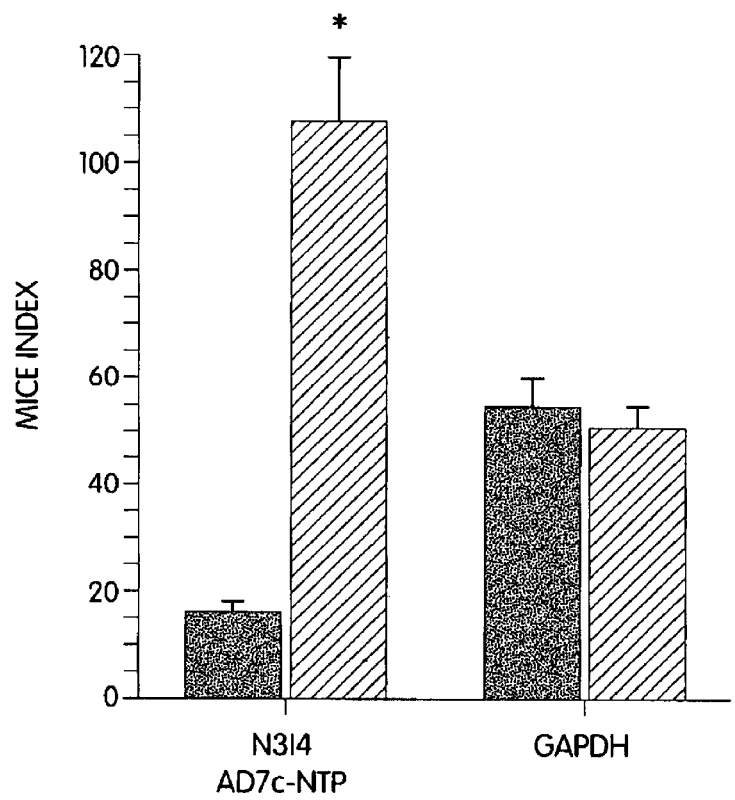
FIG. 1B is a bar graph showing the results of a AD7c-NTP and glyceraldehyde-3-phosphate dehydrogenase (GADPH) immunoreactivity in AD7c-NTP-transfected cells in the absence (solid bars) or presence of 3 mM IPTG. The MICE index reflects levels of immunoreactivity corrected for cell density. ($P<0.001$ by Student T-test analysis).

PNET2 cells were stably transfected with the AD7c-NTP cDNA using the LacSwitch II vector system (Stratagene, La Jolla, Calif.) in which gene expression was regulated by the LacZ promoter and induced by IPTG stimulation (1–5 mM). Control cells were similarly transfected with a cDNA that encodes the chloramphenicol acetyl transferase (CAT) gene. The clones selected for study exhibited tight regulation of gene expression since in the absence of IPTG, AD7c-NTP expression or Cat activity were either very low level or undetectable. IPTG stimulation induced AD7c-NTP gene expression or CAT activity, which was sustained for up to 96 hours. Optimum induction of gene expression was observed with 3 mM IPTG. Western blot analysis demonstrated substantially increased levels of the ~41 kD N3I4-immunoreactive AD7c-NTP protein in cells transfected with the AD7c-NTP cDNA relative to CAT-expressing control cells (FIG. 1A). Using the MICE assay to also measure immunoreactivity, IPTG stimulation (3 mM) resulted in nearly a five-fold increase in N3I4-immunoreactive NTP, but no change in the levels of GAPDH (FIG. 1B). Corresponding with the results of Western blot analysis, control cells (CAT gene transfected) did not exhibit IPTG-inducible NTP expression, and GAPDH expression was also unchanged by IPTG stimulation. However, CAT activity was substantially increased by IPTG induction of the CAT reporter gene in those cells.

Effects of Different Growth Factors on the Viability and Morphology of Neuronal Cells Induced to Over-express the AD7c-NTP Gene Over-expression of AD7c-NTP gene resulted in reduced neuronal cell viability and neuritic sprouting in the same cultures. Analysis of the amino acid subsequence of the translated AD7c-NTP cDNA indicated the presence of an insulin/IGF1 hybrid domain (amino acids 2–14 of SEQ ID NO:2), which suggested that the effects of AD7c-NTP over-expression might be linked to growth factor stimulation. Therefore, studies were undertaken to determine if the morphological features of neuronal cells that over-express the AD7c-NTP cDNA were regulated by differential responses to growth factors.

Cells were serum-starved for 24 hours. However, since several hours of IPTG stimulation were required to induce AD7c-NTP gene expression or CAT activity, IPTG (3 mM) was added to the cultures after 16 hours of serum-starvation, i.e. 8 hours prior to growth factor stimulation. The cells were stimulated with insulin (50 nM), IGF-1 (5 ng/ml), NGF (2.5 ng/ml), or PDGF (5 ng/ml) and examined by phase contrast microscopy 24–48 hours later. PNET2 cells could be maintained in serum-free medium for 5 to 7 days with insulin, IGF-1, NGF, or PDGF as the only growth stimulus. In addition, each of these growth factors supports DNA synthesis and promotes modest outgrowth of multipolar neurites in PNET2 cells.

The CAT-expressing control cells exhibited modest degrees of neuritic sprouting with insulin, IGF-1, PDGF, or NGF stimulation in non-transfected PNET2 cells. In contrast, PNET2 cells that were induced to express AD7c-NTP manifested different morphological responses depending upon the growth factor used. Insulin stimulation resulted in neurite retraction, cell rounding and increased cell death (floating and refractile), whereas PDGF or NGF stimulation resulted in extensive neuritic growth with multipolar fine interconnecting processes and minimal evidence of on-going cell death. NGF stimulation had the same effect on cellular morphology as PDGF. The IGF-1 stimulated cultures contained two populations of cells: some were rounded, refractile, and floating, while others were cytologically intact and exhibited prominent neuritic processes following FCS stimulation of AD7c-NTP transfected cells. It is noteworthy that IGF-1 is a major growth factor present in FCS.

Figure 2:
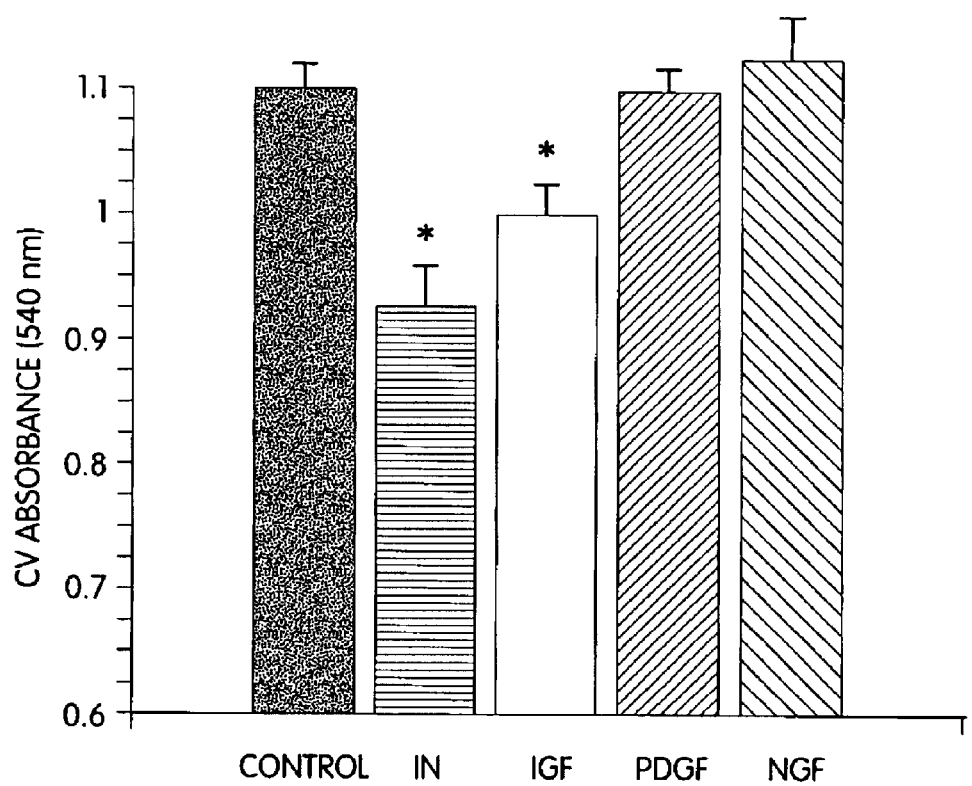
FIG. 2 is a bar graph showing reduced viability in insulin (IN) and IGF1 (IGF) stimulated cultures induced to express AD7c-NTP. Asterisks indicate significant differences form control (uninduced, FCS stimulated), or IPTG-induced, PDGF or NGF stimulated cultures as demonstrated by ANOVA ($P<0.05$).

Increased Cell Loss Associated with Insulin-stimulation and AD7c-NTP Over-expression Cell viability was quantified using the microculture Crystal violet assay with cells seeded into 96-well plates. Insulin or IGF-1 stimulation of cultures induced to express AD7c-NTP resulted in significantly reduced cell densities relative to un-induced FCS-stimulated cultures, and IPTG-induced cultures that were stimulated with NGF or PDGF (FIG. 2). The insulin-stimulated cultures had the lowest mean cell densities, and the IGF-1 stimulated cultures had mean cell densities intermediate between the insulin-stimulated and the NGF or PDGF-stimulated cultures, consistent with the observations by phase contrast microscopy. These results were not due to differences in DNA synthesis since the levels of proliferating cell nuclear antigen (PCNA) expression were similar among the cultures. Control cultures that were induced to express CAT activity and stimulated with insulin, IGF-1, NGF or PDGF had similar mean cell densities.

Analysis of Pro-apoptosis and Survival Gene Expression

Apoptosis of PNET2 cells was found to be mediated by increased levels of p53 and p21, reduced levels of Bcl-2. To determine if the insulin- and IGF-1-associated PNET2 cell death were mediated by these mechanisms, the levels of p53, Bcl-2, and p21/Waf-1 expression was measured by Western blot analysis or the MICE assay. The effects of PDGF and NGF were similar. Stimulation with insulin, IGF-1 or PDGF resulted in similar levels of the ~41 kD AD7c-NTP protein as demonstrated by Western blot analysis. Analysis of the same cell lysates demonstrated high levels of p53 and virtually undetectable Bcl-2 expression in the insulin-stimulated cultures, intermediate levels of p53 and Bcl-2 in IGF-1-stimulated cultures, and no detectable p53 and high levels of Bcl-2 in PDGF-stimulated cultures. In contrast, growth factor stimulated control cells manifested high levels of Bcl-2 and low levels of p53 expression as reported previously. The insulin-stimulated cultures also had increased levels of p21/Waf1 by Western blot analysis.

Analysis of Other Genes Associated with Cell Loss in Alzheimer's Disease

Figure 3A:
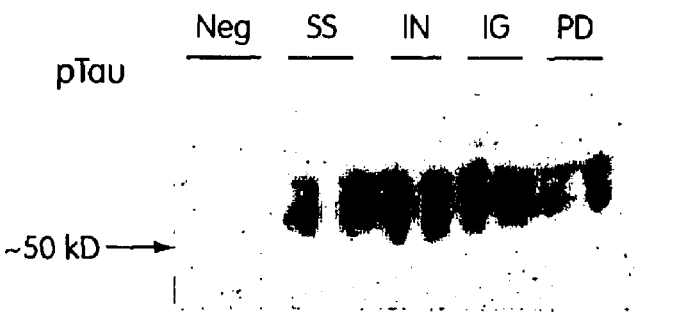
FIG. 3A is a photograph of the results of a Western Blot assay showing modulation of phospho-tau expression in PNET2 cells induced to express AD7c-NTP.
Figure 3B:
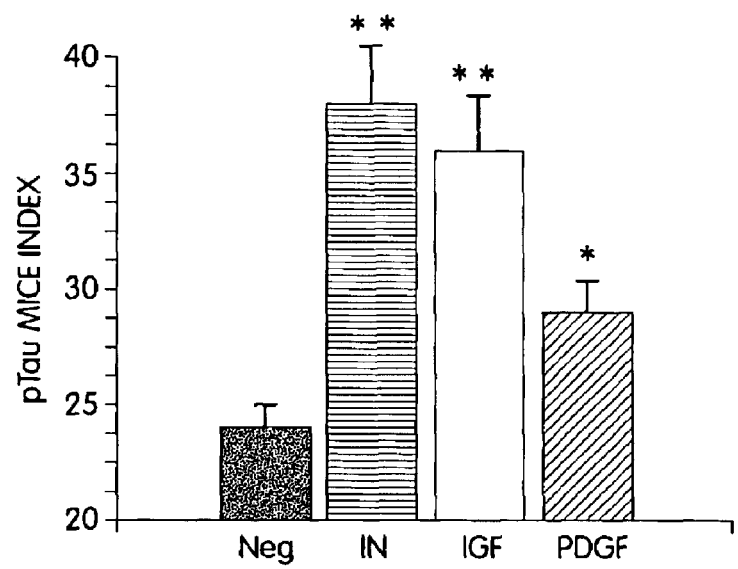
FIG. 3B is a bar graph showing showing modulation of phospho-tau expression in PNET2 cells induced to express AD7c-NTP. The data was obtained The data was obtained using the MICE assay with a monoclonal antibody which binds to phospho-tau. The graph reflects the mean±S.D. of the levels of immunoreactivity corrected for cell density (MICE Index). Asterisks indicate significant differences in the mean levels of immunoreactivity relative to control (**$P<0.001$; *$P<0.01$) by ANOVA.
Figure 3C:
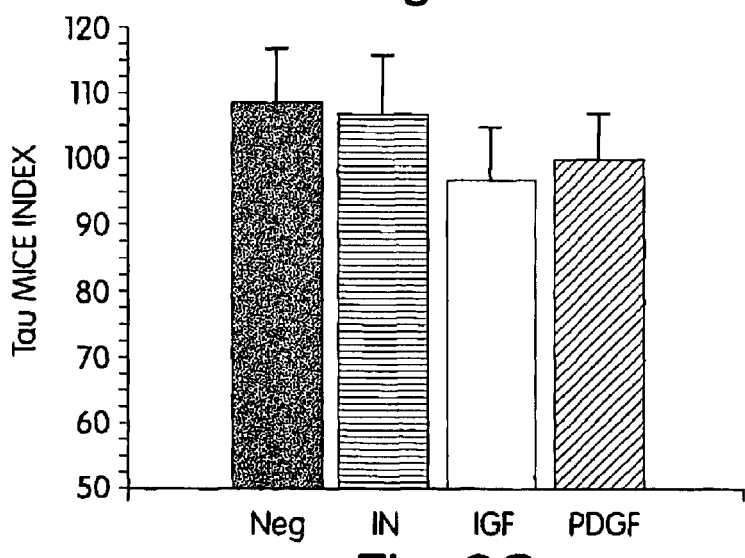
FIG. 3C is a bar graph showing showing modulation of total tau expression in PNET2 cells induced to express AD7c-NTP. The data was obtained using the MICE assay and a polyclonal antibody with binds to total tau. The negative control cells (Neg) were transfected with the AD7c-NTP cDNA but not treated with IPTG. The graph reflects the mean±S.D. of the levels of immunoreactivity corrected for cell density (MICE Index). Asterisks indicate significant differences in the mean levels of immunoreactivity relative to control (**$P<0.001$; *$P<0.01$) by ANOVA.

In addition to the activation of pro-apoptosis genes, cell loss in Alzheimer's Disease is associated with increased levels of phospho-tau, nitric oxide synthase-3 (NOS-3), and the p25 constitutive activator of cyclin dependent protein kinase 5 (Cdk5). Experiments were then carried out to determine if the expression of any of these molecules was modulated by AD7c-NTP over-expression and specific growth factor stimulation. Cells induced to express AD7c-NTP or the CAT gene and stimulated with insulin, IGF-1, or PDGF were examined for tau, phospho-tau, NOS-3, Cdk5, and p25 expression by Western blot analysis and the MICE assay. IPTG induction of the CAT gene did not result in increased expression of any of these molecules, regardless of which growth factor was used to stimulate the cells. In contrast, Western blot analysis demonstrated that cells which were induced to express AD7c-NTP and stimulated with insulin or IGF-1 exhibited increased levels of phospho-tau (FIGS. 3A–C), NOS-3, and p25 relative to corresponding cultures stimulated with PDGF, whereas the levels of tau and Cdk5 protein were not modulated in relation to growth factor stimulation.

Figure 4A:
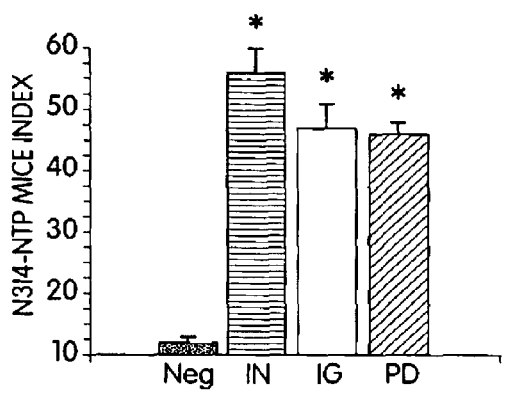
FIGS. 4A–F bar graphs showing the results of Western Blot assays. The expression levels of AD7c-NTP (FIG. 4A), p53 (FIG. 4B), p21/Waf1 (FIG. 4C), Bcl-2 (FIG. 4D), p25 (FIG. 4E), and Cdk5 (FIG. 4F) are shown for cells in insulin (IN), IGF1 (IG), PDGF (PD)-stimulated cultures induced to express AD7c-NTP by exposure to 3 mM IPTG. The negative control cultures were stimulated with 5% FCS and not exposed to IPTG. Immunoreactivity was quantified using the microtiter immunocytochemical ELISA (MICE) assay. The MICE indices correspond to the levels of immunoreactivity corrected for cell density. Graphs depict mean±S.D. of immunoreactivity measured in 16 replicate culture wells. All experiments were repeated at least 3 times. Asterisks indicate significant differences relative to the negative control values using ANOVA and Fisher's LSD post-hoc testing (*$P<0.001$; *$P<0.001$).
Figure 4D:
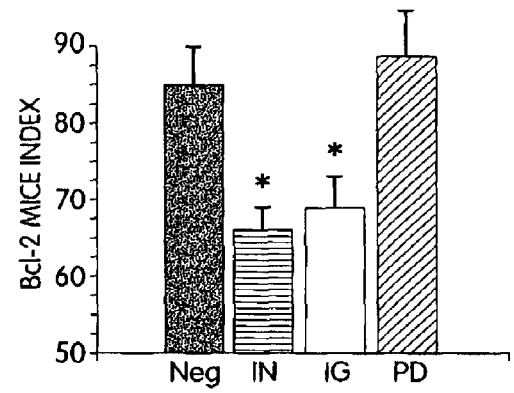
Figure 4B:
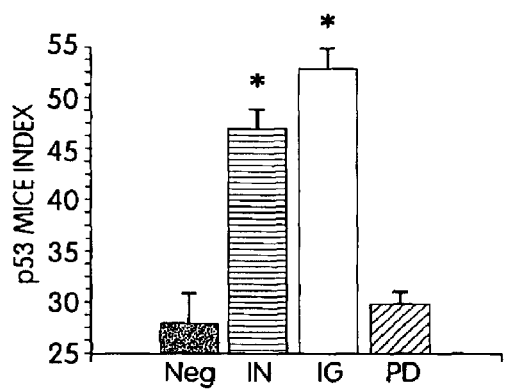
Figure 4E:
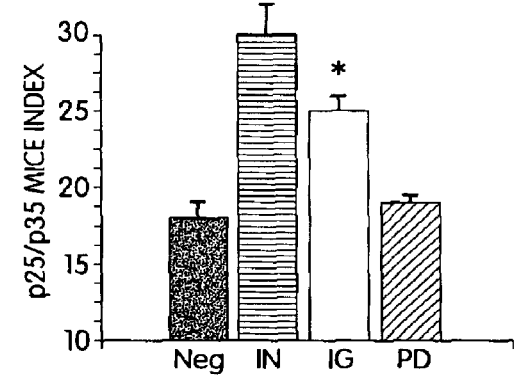
Figure 4C:
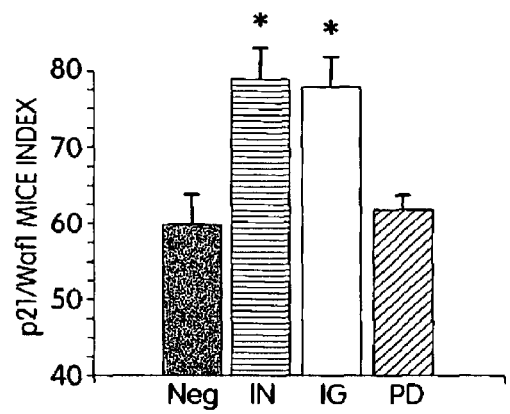
Figure 4F:
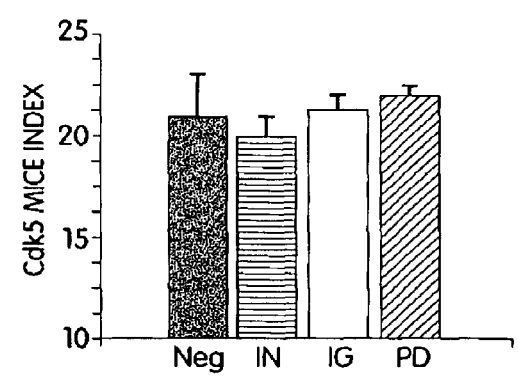

Using the MICE assay to also measure immunoreactivity, similar increased levels of N3I4-immunoreactive NTP were demonstrated in cultures stimulated with insulin, IGF-1, or PDGF (FIG. 4A), corresponding with the results of Western blot analysis described above. In addition, the MICE assay studies confirmed the significantly increased levels of p53, p21/Waf1, and p25 expression, and reduced levels of Bcl-2 in cells induced to express AD7c-NTP and stimulated with insulin or IGF-1 (FIGS. 4A–F). Although the antibody used to detect p25 could also detect p35, p35 was not detected by Western blot analysis, probably due its short half-life. The levels of Cdk5 protein were similar among the cultures and did not vary significantly with growth factor stimulation (FIG. 4F).

Analysis of Growth Factor Stimulated Activated Erk MAPK and Activated JNK Expression The potential mechanisms by which the differential effects of insulin, IGF1 and PDGF might occur were explored by examining pathways, which mediate PNET2 neuronal apoptosis and neuritic sprouting. Both ethanol and oxidative stress-induced apoptosis of PNET2 cells are associated with increased levels of phospho-JNK and reduced levels of PI3 kinase activity, whereas DNA neuritic sprouting is associated with increased levels phospho-Erk MAPK. Western blot analysis was performed with cell lysates obtained from cultures stimulated with insulin, IGF1, or PDGF for 0–30 minutes or 24 hours with equivalent protein loading (60 μg/sample). The membranes were probed using antibodies to Erk, phospho-Erk, Jun, and phospho-JNK. While the levels of total Erk and Jun were found to be similar for all samples, striking differences in the levels of growth factor stimulate phospho-Erk and phospho-JNK were detected. Insulin and IGF-1 stimulation resulted in increased levels of phosph-Erk p42/p44, with peak levels detected within 10 or 15 minutes after adding these growth factors to the medium, whereas PDGF had minimal effect on the levels of phospho-Erk MAPK in short-term stimulation experiments. In contrast, after 24 hours of AD7c-NTP gene induction and growth factor stimulation, high levels of phospho-Erk MAPK were detected in the IGF-1 and PDGF-stimulated cultures, but not in the serum-starved or insulin-stimulated cultures. Short-termed stimulation (5–30 min) with insulin also resulted in sharply increased and sustained elevations in the levels of phospho-JNK, whereas IGF-1 and PDGF stimulation were associated with much lower levels of phospho-JNK in short-term studies, and no detectable phospho-JNK expression at the 24 hour time point. Further studies demonstrated no significant differences in the levels of activated p38/HOG1 with respect to the different growth factors, consistent with observations that p38 stress kinase was not an important mediator of apoptosis in PNET2 cells. In contrast, the levels of c-fos transcription factor were equally expressed after 24 hours IPTG induction of AD7c-NTP expression and either serum starvation or stimulation with insulin, IGF1 or PDGF.

Analysis of Growth Factor Stimulated PI3 Kinase Activity

PI3 kinase is an important mediator of neuronal survival. The pro-survival effects of PI3K are mediated through activation of Akt (protein kinase B) and phosphorylation of Bad to render it inactivated. Inhibition of PI3 kinase activity is associated with PNET2 cell apoptosis. Therefore, experiments were carried out to determine if growth factor stimulated PI3 kinase activity was inhibited in insulin or IGF-1-stimulated cultures. Such inhibition has been observed following chronic ethanol exposure. Since insulin and IGF-1 can activate PI3 kinase through the insulin-receptor substrate-1 (IRS-1) or through IRS-1-independent pathways, both IRS1-associated PI3 kinase and total PI3 kinase activities were measured. These studies were conducted using insulin or PDGF stimulated cultures in which AD7c-NTP gene expression was induced by 3 mM IPTG stimulation. IRS-1-associated PI3 kinase activity was sharply increased by insulin but not PDGF stimulation. High levels of IRS-1-associated PI3 kinase activity were detected throughout the 30 minutes of insulin stimulation, whereas in the PDGF-stimulated cultures, IRS-1-associated PI3 kinase activity was virtually undetectable. To examine total PI3 kinase activity, the levels of p85 subunit bound to phospho-tyrosine was examined by immunoprecipitation/Western blot analysis. Levels of PI3 kinase activity were measured in anti-phospho-tyrosine (PY) immunoprecipitates. The immunoprecipitation/Western blotting studies demonstrated similarly high levels of PY-associated p85 (subunit of PI3K), both after 5–30 minutes and 24 or 48 hours of growth factor stimulation. Similarly, PI3 kinase activity was readily detected in the PY immunoprecipitates prepared with cells stimulated with insulin or PDGF. Of interest was that for the short-term studies, the levels of PY-PI3 kinase activity were consistently lower in the PDGF-stimulated than in the insulin-stimulated cultures, whereas the levels of PY-PI3 kinase activity were similar after 24 or 48 hours of insulin or PDGF stimulation.

Growth Factor-induced Apoptosis and Neuritic Sprouting with Over-expression of the Alzheimer's Disease Associated Neural Thread Protein Gene The AD7c-NTP gene is over-expressed in brains with Alzheimer's disease at early and intermediate stages of neurodegeneration. AD7c-NTP immunoreactivity co-localizes with early phospho-tau immunoreactive cytoskeletal lesions in brains with AD, and increased levels of phospho-tau and AD7c-NTP in cerebrospinal fluid correlate with the severity of Alzheimer's Disease dementia. Prior to the invention, it was difficult to investigate the role of AD7c-NTP using standard stably transfected clones due to progressive depletion of the cells in culture. Therefore, we an inducible mammalian expression vector system was developed to regulate AD7c-NTP expression in human CNS-derived PNET2 neuronal cells in which gene expression was induced by the addition of IPTG to the medium, and inhibited by withdrawal of IPTG. IPTG-induced gene expression (AD7c-NTP or CAT activity) was detectable within 8 hours and sustained for up to 96 hours. The effects of AD7c-NTP over-expression was examined using 6 clones that had tightly regulated inducible gene expression whereby in the absence of IPTG, expression of the ~41 kD N3I4-immunoreactive AD7c-NTP protein was virtually undetectable.

In all 6 clones that were stably transfected with the AD7c-NTP cDNA, IPTG stimulation substantially increased AD7c-NTP expression as demonstrated by Western blot analysis and the MICE assay. In contrast, the expression of a non-relevant gene, GAPDH, was unchanged by IPTG stimulation. Within 24 hours of IPTG stimulation, the expected ~41 kD AD7c-NTP protein was easily detected by Western blot analysis, whereas in control cells induced to express the CAT gene, AD7c-NTP immunoreactivity was either very low level or undetectable. The MICE assay was used to quantify AD7c-NTP expression in the presence or absence of IPTG stimulation. The MICE assay provides a more sensitive measure of immunoreactivity and permits simultaneous analysis of multiple cultures under the same conditions without requiring protein extraction or gel electrophoresis. Importantly, the levels of immunoreactivity are corrected for cell density in the calculation of the MICE index. Using the MICE assay, we confirmed the presence of very low levels of N3I4-immunoreactive AD7c-NTP in un-induced PNET2 cells, and a greater than five-fold increase in the mean levels of N3I4-immunoreactive AD7c-NTP expression after 24 hours of IPTG induction of gene expression.

The role of growth factor stimulation was examined in relation to the morphological features associated with AD7c-NTP over-expression based upon the presence of an insulin/IGF1 chimeric receptor domain predicted by subsequence analysis of the translated cDNA. Empirical studies demonstrated that in PNET2 cells induced to express AD7c-NTP, insulin stimulation resulted in neurite retraction, cell rounding, and progressive cell death, whereas IGF-1 stimulation reproduced the dimorphic cell populations of apoptotic and sprouting neurons originally described in fetal calf serum stimulated stably transfected cultures. In contrast, NGF or PDGF stimulation resulted in prominent multipolar outgrowth of neuritic processes corresponding to a predominantly sprouting phenotype. These effects were not due to differences in the levels of AD7c-NTP expression because the levels of AD7c-NTP protein detected by Western blot analysis and the MICE assay were similar under all growth factor stimulation conditions.

The increased PNET2 cell death observed with insulin or IGF1 stimulation was associated with increased expression of the p53 pro-apoptosis gene product and reduced expression of the Bcl-2 survival gene. In addition, higher levels of p21/Waf1, through which p53 frequently signals to mediate apoptosis, occurred in insulin and IGF-1 stimulated cultures. The insulin-stimulated cells also had increased levels of phospho-JNK relative to IGF-1- and PDGF-stimulated cultures, both in the short-term (5–60 min) and long-term (24 hrs) stimulation studies. p53-induced apoptosis can be mediated by signaling through the jun B/JNK pathway. In contrast to previous studies in which ethanol or oxidative stress induced neuronal apoptosis was found to be partly due to inhibition of growth factor-stimulated PI3 kinase activity, both IRS-1-associated and PY-associated (total) PI3 kinase activities were abundantly (normally) stimulated by insulin as reported in non-transfected PNET2 cells. Therefore, the increased cell death observed in the insulin-stimulated cultures could not be attributed to inhibition of PI3 kinase activity. Although the insulin-stimulated Erk MAPK pathway was also intact following short-term stimulation, the reduced levels of phospho-Erk MAPK detected after 24 hours of insulin stimulation correlate with the neurite retraction observed in those cultures. Erk MAPK activation can mediate neuritic sprouting as occurred following IGF-1-, NGF-, or PDGF-stimulation.

These alterations in gene expression and intracellular signaling effected by AD7c-NTP over-expression and insulin or IGF1 stimulation mimic responses associated with oxidative stress. In the insulin- and IGF-1-stimulated cultures, PNET2 neuronal cell death was also associated with increased levels of nitric oxide synthase-3 (NOS3), phospho-tau, and the p25 regulatory partner of cyclin dependent kinase 5 (Cdk-5). Each of these molecules is expressed at increased levels in brains with Alzheimer's Disease. NOS3 expression, like AD7c-NTP, is aberrantly increased in Alzheimer's Disease cortical neurons and dystrophic neurites beginning early in the course of neurodegeneration. Intra-neuronal phospho-tau-immunoreactive cytoskeletal lesions are a major hallmark of Alzheimer's Disease-associated neurodegeneration as their densities correlate with severity of dementia.

In Alzheimer's Disease, Cdk5 activity is increased due to increased neuronal levels of p25. In the brain, Cdk5 kinase activity is regulated by interaction with p35, or its truncated, catalytically active C-terminal fragment, p25. p35 has a short half-life, which may be important for the on-off regulation of Cdk5 kinase activity. In contrast, p25 is highly stable and over-expression of p25 leads to constitutive activation of Cdk5 kinase and also promotes apoptosis. Tau and neurofilament proteins can be phosphorylated by Cdk5 kinase, and in brains with Alzheimer's Disease, p25 immunoreactivity and cdk5 kinase activity co-localize with degenerating neurons and cell processes that contain phospho-tau immunoreactive cytoskeletal lesions. Therefore, over-expression of AD7c-NTP in neuronal cells stimulated with insulin or IGF-1 results in increased levels of both phospho-tau and p25, which have already been mechanistically linked to AD-type neurodegeneration.

The levels of NOS-3 expression were also increased in insulin or IGF-1 stimulated cells induced to express AD7c-NTP. NOS-3 over-expression is a feature of Alzheimer's Disease as well as other neurodegenerative diseases. High levels of NOS-3 can lead to increased levels of NO and oxidative injury, and some data indicate that oxidative injury to neuronal cells can promote tau phosphorylation and the conversion of p35 to p25. Constitutive over-expression of the NOS-3 cDNA in PNET2 neuronal cells is sufficient to cause apoptosis associated with increased levels of p53, reduced levels of Bcl-2, increased p35-to-p25 conversion, and tau phosphorylation. These results indicate that AD7c-NTP-induced neuronal apoptosis is mediated by oxidative injury due to attendant increases in the levels of NOS-3 expression. In Alzheimer's Disease brains, aberrant expression of both NOS-3 and AD7c-NTP begins early, involves the same structures, and is intimately associated with apoptotic cell loss and neurodegeneration.

The AD7c-NTP protein has a hydrophobic leader sequence (residues 1–15 of SEQ ID NO:2) and at least one transmembrane domain. For example, seven putative transmembrane domains are located within the AD7c-NTP protein (residues 70–92, 111–18, 126–134, 147–177, 182–191, 241–249, and 339–351 of SEQ ID NO:2). The insulin/IGF1 chimeric receptor motif is located at the amino terminus (residues 2–14 of SEQ ID NO:2) and can be exposed to the cell surface, rendering it accessible to interactions with extracellular growth factors. Alternatively, insulin and IGF-1 signaling through one of the insulin receptor substrates (IRS) such as IRS-1 or IRS-2 which are both expressed in neuronal cells may mediate the observed effects in the context of AD7c-NTP over-expression. For example, insulin stimulation of ethanol exposed neuronal cells causes apoptosis, whereas NGF stimulation rescues the cells from ethanol-induced apoptosis and also promotes neuritic sprouting.

The mechanisms involved in the insulin-stimulated pro-apoptosis signaling and NGF-mediated rescue are distinct from those identified in relation to AD7c-NTP over-expression. Since insulin, IGF-1, NGF, and PDGF can support growth and promote neuritic sprouting in PNET2 cells, the data described herein indicates that AD7c-NTP over-expression alters or impairs insulin- and IGF-1-stimulated signaling mechanisms in neuronal cells. The adverse effects of AD7c-NTP expression on intracellular signaling appear to be selective with respect to growth factor stimulated neuronal survival and anti-apoptosis mechanisms. Both insulin and IGF-1 stimulation of cells induced to over-express AD7c-NTP exhibited prominent activation of pro-apoptosis mechanisms and inhibition of survival pathways. The finding that NGF and PDGF-stimulated survival mechanisms were preserved indicates that in the context of AD7c-NTP over-expression, the IRS-activated pathways may be particularly vulnerable. IGF-1 and insulin transmit signals by receptor tyrosine kinase activation of both IRS-dependent and IRS-independent pathways, while NGF and PDGF transmit intracellular signals through IRS-independent mechanisms. These results indicate that CNS neuronal cells that over-express the AD7c-NTP gene are rescued and encouraged to exhibit neuritic sprouting and re-establish connections by exogenous stimulation with NGF or PDGF. Loss of cells that produce NGF or PDGF in Alzheimer's Disease precipitates an AD7c-NTP-associated cascade of neurodegeneration.

EXAMPLE 2

AD7c-NTP Induced Neurodegeneration

A method to efficiently transfect postmitotic primary neuronal cell cultures was developed and used to demonstrate that over-expression of the AD7c-NTP gene causes both increased cell death and neuritic sprouting, which are two of the prominent abnormalities associated with Alzheimer's Disease. These results indicate that aberrantly increased AD7c-NTP NTP expression has a role in Alzheimer's Disease-type neurodegeneration. Primary postmitotic neurons were efficiently transfected with conventional recombinant plasmid DNA to evaluate the effects of gene over-expression in the context of neurodegeneration using art-recognized in vitro models.

In vitro Model

Post-mitotic primary rat cerebellar neuron (rCBN) cultures were generated with brain tissue derived from postnatal day 6 pups. Five-day-old cultures were transfected with the full length AD7c-NTP cDNA (pcDNA3-AD7c) or the luciferase (pcDNA3-Luc) or LacZ (pcDNA3-beta-Gal) reporter gene ligated into the pcDNA3.1 vector (Invitrogen) in which gene expression was regulated by a CMV promoter. Cells seeded into 6-well or 96-well plates were transfected using IT-100 or LT-1 Mirus transfection reagent (Panvera) following the manufacturer's protocol. Transfection efficiency ranged from 10% to 25% as demonstrated by co-transfection with recombinant plasmid DNA expressing green fluorescent protein (pcDNA3-GFP) and visualizing the percentage of labeled cells by fluorescence microscopy. The cells were analyzed for gene expression, viability, and morphology 24, 48, or 72 hours after transfection.

Viability Assays

Viability was measured by a standard crystal violet assay. The assays were performed with cells seeded into 96-well plates at a density of $2 \times 10^4$ cells/well. The absorbances were measured using a Spectracount plate reader (Packard, Meriden, Conn.). The crystal violet absorbances increased linearly with cell density between 104 and $5 \times 10^5$ cells/well.

Protein Expression

Western blot analysis, the microtiter immunocytochemical ELISA (MICE) assay, and immunocytochemical staining were used to measure protein expression. For Western blot analysis, the cells were lysed in radioimmunoprecipitation assay buffer supplemented with protease and phosphatase inhibitors. Protein concentrations were measured using the BCA assay (Pierce Chemical Company, Rockford, Ill.). Samples containing 60 $\mu$g of protein were analyzed by Western immunoblotting as described previously.

The MICE assay is a rapid and sensitive method for quantifying immunoreactivity in 96-well micro-cultures and combines the advantages of the enzyme-linked immunosorbant assay with immunocytochemical staining to permit sensitive in situ quantification of protein expression with values normalized to cell density. Briefly, the cells were fixed in Histochoice (Amresco, Solon, Ohio), permeabilized with 0.05% saponin in Tris-buffered saline (50 mM Tris, pH 7.5, 0.9% NaCl; TBS), and blocked with Superblock-TBS (Pierce, Rockford, Ill.). The cells were then incubated overnight at 4° C. with primary antibody diluted in TBST-BSA. Immunoreactivity was detected using horseradish peroxidase conjugated secondary antibody (Pierce, Rockford, Ill.) and the TMB soluble peroxidase substrate (Pierce, Rockford, Ill.). Absorbances were measured at 450 nm using a Spectracount plate reader (Packard Instrument Company, Meriden, Conn.). Relative culture cell density was determined by subsequently staining the cells with 0.1% Coomassie blue dye, lysing the labeled cells with 1% SDS, and measuring the absorbances of at 540 nm. The MICE index was calculated from the ratio of the absorbances measured for immunoreactivity and cell density. Eight or 16 replicate culture wells were analyzed in each experiment. All experiments were repeated at least 3 times.

For immunocytochemical staining, adjacent culture wells were pretreated and incubated with primary antibody as described for the MICE assay. Immunoreactivity was revealed using biotinylated secondary antibody and avidin-biotin horseradish complex (ABC) reagents (Vector Laboratories, Burlingame, Calif.). Immunoreactivity was revealed using diaminobenzidine as the chromogen.

Effective Gene Transfer into rCBN Cultures

Figure 5:
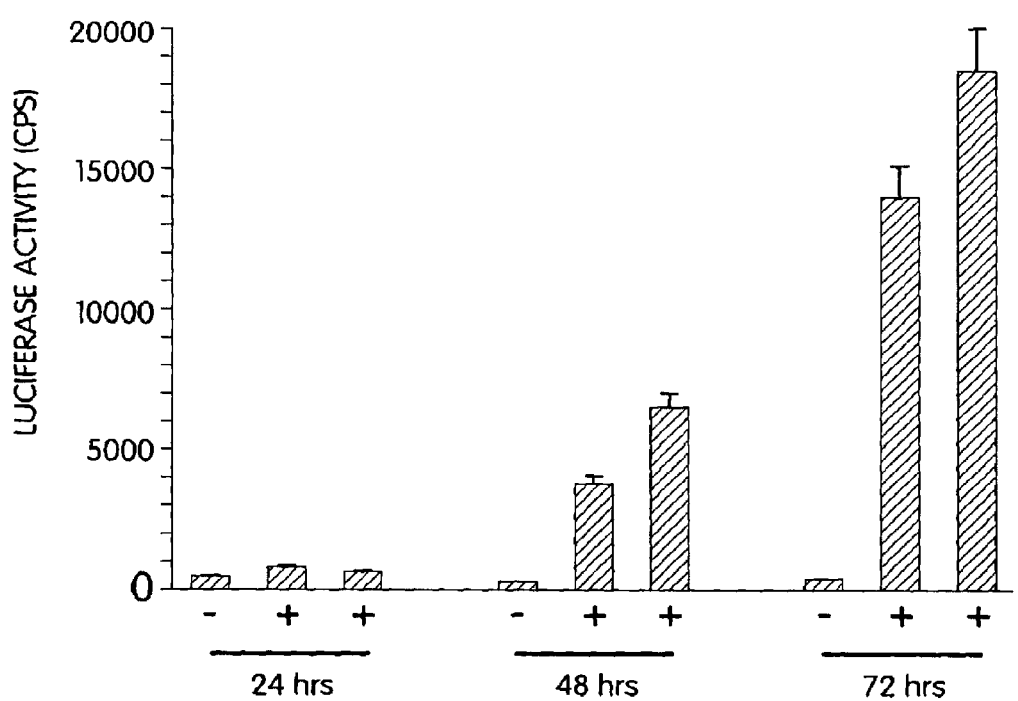
FIG. 5 is a bar graph showing detection of luciferase activity in rat cerebellar neuron cultures transfected with pcDNA3-Luc (+) or pcDNA3-AD7c (−) using a polyamine composition. Values graphed represent the mean±S.D. of results obtained from 4 replicate culture wells per time point.
Figure 6A:
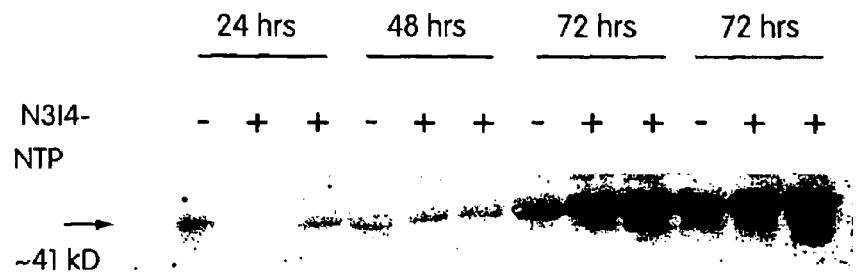
FIG. 6A is a photograph of the results of a Western Blot assay showing the detection of AD7c-NTP expression in rat cerebellar neuron cultures transfected with pcDNA3-Luc (−) or pcDNA3-AD7c (+) using a polyamine compositions. The arrow indicates the position of the ~41 kD n3I4-immunoreactive AD7c-NTP protein.
Figure 6B:
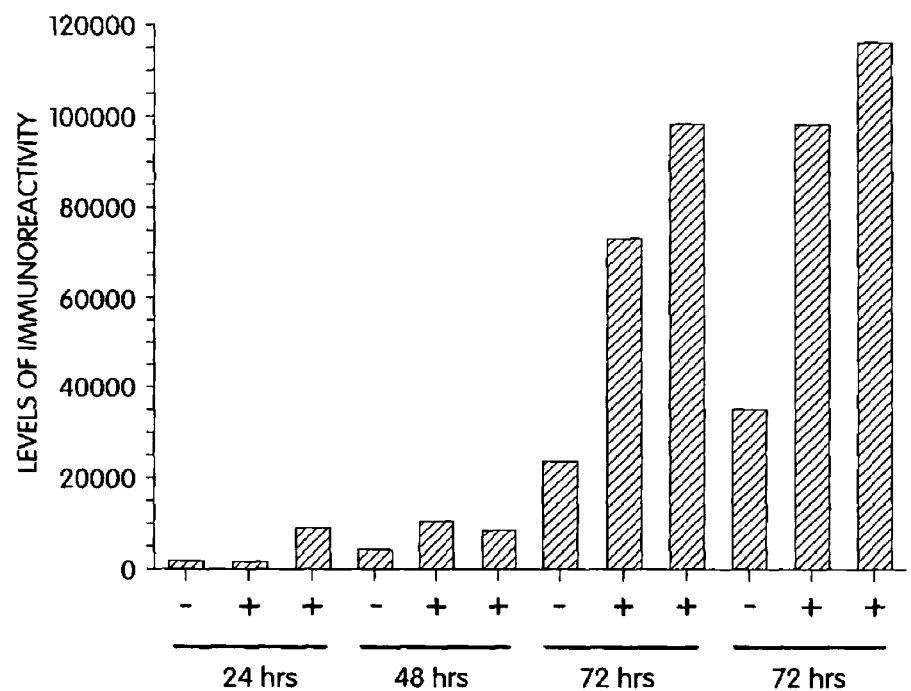
FIG. 6B is a bar graph of a densitometric quantification of the data shown in FIG. 6A.

FIG. 5 demonstrates luciferase activity in rCBN cultures transfected with pcDNA3-Luc. Increased luciferase activity was detected 48 hours after transfection, and at the 72-hour time point, the levels were further increased. Western blot analysis using an AD7c-NTP specific monoclonal antibody generated to recombinant AD7c-NTP protein, demonstrated increased levels of the ~41 kD AD7c-NTP protein in cells transfected with pcDNA3-AD7c relative to cells transfected with pcDNA3-Luc (FIG. 6A). Densitometric analysis of the autoradiographs showed that transfection with pcDNA3-AD7c resulted in three- to five-fold higher levels of AD7c-NTP protein relative to the pcDNA3-Luc control transfected cells at the 72-hour time point (FIG. 6B). Using the MICE assay and monoclonal antibodies to quantify AD7c-NTP immunoreactivity, substantially increased levels of AD7c-NTP expression were measured in rCBN cultures, both 48 and 72 hours after transfection with pcDNA3-AD7c relative to control transfected cultures. Further studies revealed progressive reductions in the levels of enzyme activity or gene expression between 4 and 7 days after transfection. Similar results were generated in at least four separate experiments.

Effects of AD7c-NTP Over-expression on Neuronal Viability and Morphology

Viability was measured using the crystal violet assay. Over-expression of AD7c-NTP cDNA resulted in significant neuronal cell loss relative to the control cultures. Within 72 hours of transfection, the cultures that were transfected with pcDNA3-AD7c exhibited approximately 36% lower mean cell densities relative to control cultures. Phase contrast microscopy demonstrated progressive depletion of the granule cell neurons in cultures transfected with pcDNA3-AD7c (FIGS. 7A, B). In addition, the remaining granule cell neurons in the pcDNA3-AD7c transfected cultures exhibited prominent neuritic sprouting manifested by the presence of long thin interconnecting processes emanating from nearly all cells (FIG. 7A), compared with the short, mainly apparent cell processes in the control cultures (FIG. 7B). Immunocytochemical staining studies revealed abundant AD7c-NTP immunoreactivity, 48 and 72 hours after transfection with pcDNA3-AD7c, and relatively low levels of AD7c-NTP immunoreactivity in the corresponding control (pcDNA3-LacZ or pcDNA3-Luc) transfected cells (FIGS. 7C–F).

Neurodegeneration in Primary CNS Neurons Transfected with Alzheimer's Disease-Associated Neuronal Thread Protein Gene The data described herein demonstrates that efficient gene transfer in postmitotic neurons was achieved using a formulation containing a nucleic acid, a histone protein, liposomes, and an amphipathic compound. For example, the DNA is delivered using the MIRUS polyamine transfection reagent. Over-expression of the AD7c-NTP gene causes neuronal cell death and neuritic sprouting in postmitotic neurons. In the rCBN cultures, optimum gene expression following transfection was detected after 72 hours rather than 24 or 48 hours, as generally occurs in transfected cell lines. The advantage of using the polyamine transfection composition is that studies can now be done with primary neuronal cell cultures rather than transformed cell lines. Moreover, the effects of gene expression are determined using conventional assays rather than single cell analysis, since a sufficiently high percentage (10–25%) of the cells were found to express the gene of interest. Finally, the use of primary neuronal cell cultures provides a more relevant model for studying the effects of aberrant gene expression in relation to neurodegeneration.

These studies demonstrated that transfection of post-mitotic neurons with pcDNA3-AD7c causes increased cell death and neuritic sprouting. Over-expression of the AD7c-NTP gene was documented by Western blot analysis, the MICE assay, and immunocytochemical staining using monoclonal antibodies generated to the human recombinant protein. In contrast, transfection with non-relevant genes was associated with very low-level or undetectable AD7c-NTP expression.

Over-expression of AD7c-NTP resulted in neuronal cell death and prominent neuritic sprouting. These two phenotypes were originally observed in PNET2 neuronal cell lines that were transiently transfected with the same cDNA. However, PNET2 cells are immature, proliferative, and transformed. To determine the potential role of the AD7c-NTP gene in relation to AD-type neurodegeneration which affects post-mitotic neurons exclusively, it was necessary to demonstrate that over-expression of the AD7c-NTP gene has the same effect in post-mitotic neurons as observed previously in PNET2 cells. The phase contrast microscopy studies demonstrated progressive depletion of granule cell neurons, and prominent growth of long, thin interconnecting processes from the remaining viable neurons in the AD7c-NTP transfected cultures. The neurite outgrowth was probably not just a response to cell loss since rCBN cultures treated with oxidants exhibit similar degrees of cell loss as well as neurite retraction rather than sprouting. Over-expression of the AD7c-NTP gene may cause neuronal cell death, while exposure of neurons to extracellular (secreted) AD7c-NTP protein may promote neuritic sprouting.

EXAMPLE 3
Non-Transgenic Animal Model for Alzheimer's Disease

Studies were undertaken to evaluate the effects of AD7c-NTP over-expression in the brain using an in vivo model of gene transfer.

In AD, dementia is due to cell loss, mediated by apoptosis, impaired mitochondrial function, and possibly necrosis. A second major correlate of dementia is synaptic disconnection due to neuritic degeneration. Although several gene abnormalities are known to cause familial AD, the underlying basis of sporadic AD, which accounts for the majority of cases, has been difficult to elucideate. AD7c-NTP is over-expressed in brains with sporadic AD. Increased levels of the corresponding ~41 kD protein are detectable at early and intermediate stages of AD, and in the brain, AD7c-NTP immunoreactivity co-localizes with phospho-tau. Over-expression of the AD7c-NTP gene causes apoptosis, impaired mitochondrial function, and aberrant neuritic sprouting in cultured neuronal cells.

In vivo gene transfer methods were used to demonstrate that over-expression of AD7c-NTP in the brain causes neuronal cell loss associated with activation of pro-apoptosis genes and increased levels of phospho-tau, amyloid precursor protein, amyloid-b, and nitric oxide synthase-3 expression localized in neurons or senile plaque-like structures. Over-expression of AD7c-NTP leads to increased levels of NOS-3, which promotes chronic oxidative stress and secondary neurodegenerative changes similar to the abnormalities observed in AD.

Gene Transfer

Eight to 10 day-old Long-Evans rats anesthetized with 60 mg/kg of pentobarbital were inoculated in the right cerebral hemisphere with recombinant plasmid DNA containing the complete coding sequence of the AD7c-NTP (pAD7c-NTP), LacZ (pLacZ), or Luciferase (pLuc) cDNA. The nucleotide sequence encoding AD7c-NTP and the amino acid sequence of the gene product is known in the art (de la Monte et al., 1997, J. Clin. Invest. 100:1–12; GENBANK™ Accession No. AF010144 or NM04486).

TABLE 1

DNA encoding human AD7c-NTP

```
   1 tttttttttt tgagatggag ttttcgctct tgttgcccag gctggagtgc aatggcgcaa
  61 tctcagctca ccgcaacctc cgcctcccgg gttcaagcga ttctcctgcc tcagcctccc
 121 cagtagctgg gattacaggc atgtgcaccc acgctcggct aattttgtat ttttttttag
 181 tagagatgga gtttctccat gttggtcagg ctggtctcga actcccgacc tcagatgatc
 241 cctccgtctc ggcctcccaa agtgctagat acaggactgg ccaccatgcc cggctctgcc
 301 tggctaattt ttgtggtaga aacagggttt cactgatgtg cccaagctgg tctcctgagc
 361 tcaagcagtc cacctgcctc agcctcccaa agtgctggga ttacaggcgt gcagccgtgc
 421 ctggcctttt tattttattt ttttttaagac acaggtgtcc cactcttacc caggatgaag
 481 tgcagtggtg tgatcacagc tcactgcagc cttcaactcc tgagatcaag catcctcctg
 541 cctcagcctc ccaagtagct gggaccaaag acatgcacca ctacacctgg ctaattttta
 601 tttttatttt taattttttg agacagagtc tcaactctgt cacccaggct ggagtgcagt
 661 ggcgcaatct tggctcactg caacctctgc ctcccgggtt caagttattc tcctgcccca
 721 gcctcctgag tagctgggac tacaggcgcc caccacgcct agctaattt tttgtatttt
 781 tagtagagat ggggttcacc atgttcgcca ggttgatctt gatctctgga ccttgtgatc
 841 tgcctgcctc ggcctcccaa agtgctggga ttacaggcgt gagccaccac gcccggctta
 901 ttttttaattt tgtttgttt gaaatggaat ctcactctgt tacccaggct ggagtgcaat
 961 ggccaaatct cggctcactg caacctctgc ctcccgggct caagcgattc tcctgtctca
1021 gcctcccaag cagctgggat tacgggcacc tgccaccaca cccgctaat ttttgtattt
1081 tcattagagg cggggtttca ccatatttgt caggctggtc tcaaactcct gacctcaggt
1141 gacccacctg cctcagcctt ccaaagtgct gggattacag gcgtgagcca cctcacccag
1201 ccggctaatt tagataaaaa aatatgtagc aatgggggt cttgctatgt tgcccaggct
1261 ggtctcaaac ttctggcttc atgcaatcct tccaaatgag ccacaacacc cagccagtca
1321 catttttaa acagttacat ctttatttta gtatactaga aagtaataca ataaacatgt
1381 caaacctgca aattcagtag taacagagtt cttttataac ttttaaacaa agctttagag
1441 ca
```
(SEQ ID NO:1; GENBANK™ Accession No. NM014486)

TABLE 2

Amino acid sequence of human AD7c-NTP

MEFSLLLPRLECNGAISAHRNLRLPGSSDSPASASPVAGITGMCTHARLI

LYFFLVEMEFLHVGQAGLELPTSDDPSVSASQSARYRTGHHARLCLANFC

GRNRVSLMCPSWSPELKQSTCLSLPKCWDYRRAAVPGLFILFFLRHRCP

TLTQDEVQWCDHSSLQPSTPEIKHPPASASQVAGTKDMHHYTWLIFIFIF

NFLRQSLNSVTQAGVQWRNLGSLQPLPPGFKLFSCPSLLSSWDYRRPPRL

ANFFVFLVEMGFTMFARLILISGPCDLPASASQSAGITGVSHHARLIFNF

CLFEMESHSVTQAGVQWPNLGSLQPLPPGLKRFSCLSLPSSWDYGHLPPH

PANFCIFIRGGVSPYLSGWSQTPDLR
(SEQ ID NO:2; GENBANK™ Accession No. NM014486; insulin/IGF-1 receptor domain is underlined)

DNA was purified using endotoxin-free columns (Qiagen Inc., Valencia, Calif.). DNA (3 μg/inoculum) was formulated with a histone and an amphipathic compound (e.g., Transit In Vivo polyamine reagent (Panvera Inc., Madison, Wis.)). The DNA mixture was injected into the right lateral ventricle of a rat brain in a volume of 25 μl using a stereotactic frame and atlas. The rats were sacrificed to examine gene expression and histopathology, 1, 2, 3, 4, 7, 14, 21, or 28 days after the inoculation.

Evaluation of Tissue Samples

Western blot analysis was used to measure AD7c-NTP protein expression in cell lysates prepared in radioimmunoprecipitation assay (RIPA) buffer supplemented with protease and phosphatase inhibitors[7]. Protein concentrations were measured using the BCA assay (Pierce Chemical Company, Rockford, Ill.). Samples containing 60 μg of protein were fractionated by sodium dodecyl sulfate polyacrylamide gel electrophoresis (SDS-PAGE), then transferred to PVDF membranes, and analyzed by Western immunoblotting. Immunoreactivity was detected with horseradish peroxidase conjugated secondary IgG and PicoWest enhanced chemiluminescence reagents (Pierce Chemical Company, Rockford, Ill.), and quantified using the Kodak Digital Imager System.

To perform histological studies and in situ analysis of gene expression, the brains were sectioned in the coronal plane and either embedded in paraffin or snap frozen for cryosectioning. Histopathological studies were performed on paraffin sections stained with hematoxylin and eosin. Immunoreactivity for AD7c-NTP, pro-apoptosis genes (p53, Bax), phospho-tau, amyloid precursor protein (APP), amyloid-β (Aβ), synaptophysin, or nitric oxide synthase-3 (NOS3) was detected in adjacent paraffin sections using known methods. β-galactosidase activity was detected in cryostat sections using standard methods.

Intracerebral Expression of AD7c-NTP Following in vivo Gene Transfer

Gene transfer was made by inoculating the right lateral ventricle with recombinant plasmid DNA complexed with histone proteins and an amphipathic compound. The cerebral hemispheres were hemisected and analyzed separately for AD7c-NTP expression by Western blot analysis using an AD7c-NTP-specific monoclonal antibody (e.g., N3I4), which binds to the recombinant protein.

Figure 8A:
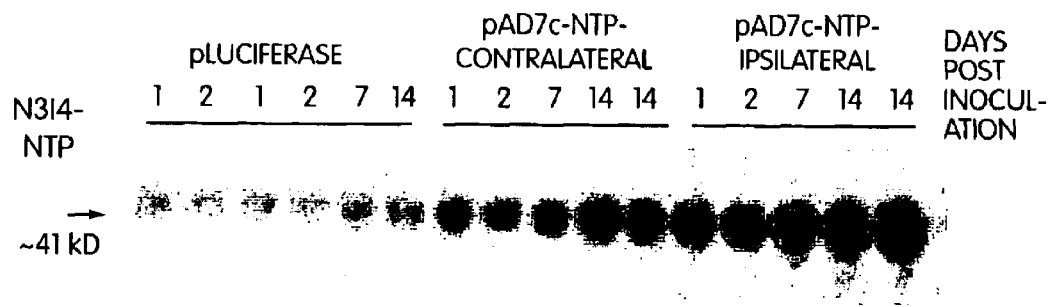
FIG. 8A is a photograph of the results of a Western Blot assay in which AD7c-NTP gene product was detected using an AD7c-NTP-specific antibody.
Figure 8B:
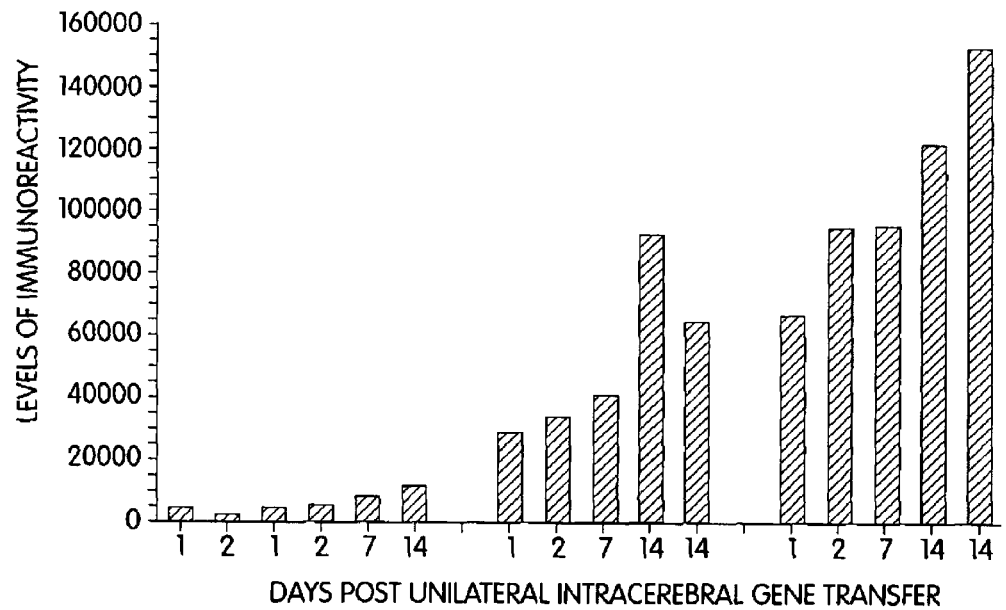
FIG. 8B is a bar graph showing the results of a densitometric quantification of the intensity of the bands detected by Western Blot assay (FIG. 8A).
Figure 9A:
FIGS. 9A–D are photographs of hematoxylin and eosin stained histological sections of brains inoculated with pLacZ (FIGS. 9A,B) or pAD7c-NTP (FIGS. 9AC, D). Brains were harvested 1 week after gene transfer. Brains inoculated with pAD7c-NTP exhibited neuronal loss with scattered pale, irregular neurons that lacked nuclei (ghost cells). The higher magnification image shown in FIG. 9C illustrates a cluster of dying neurons contained within the oval.
Figure 9B:
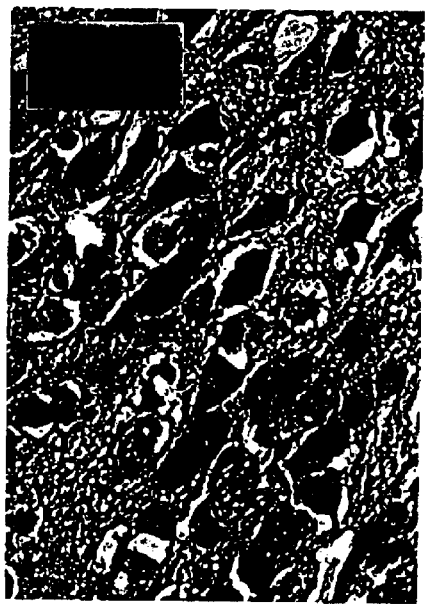
Figure 9C:
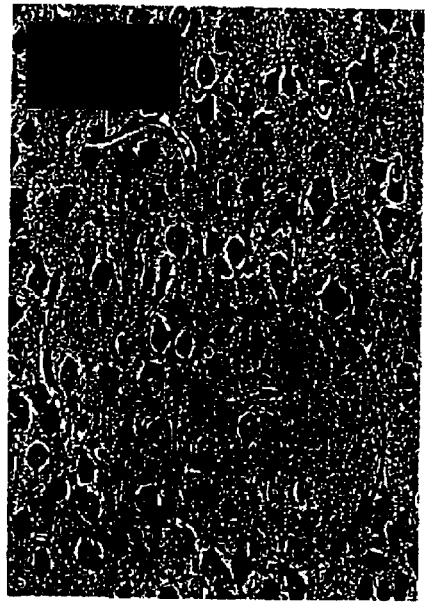
Figure 9D:
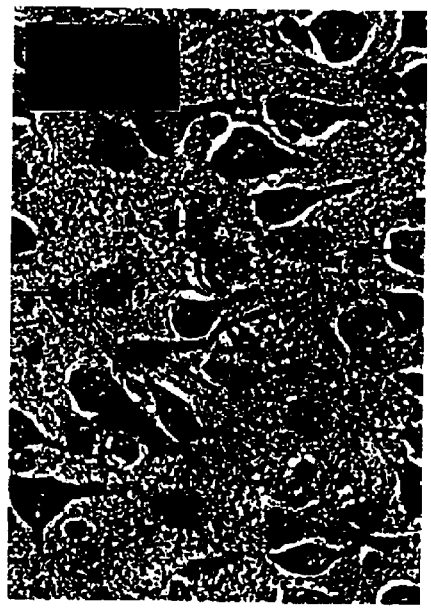
Figure 10B:
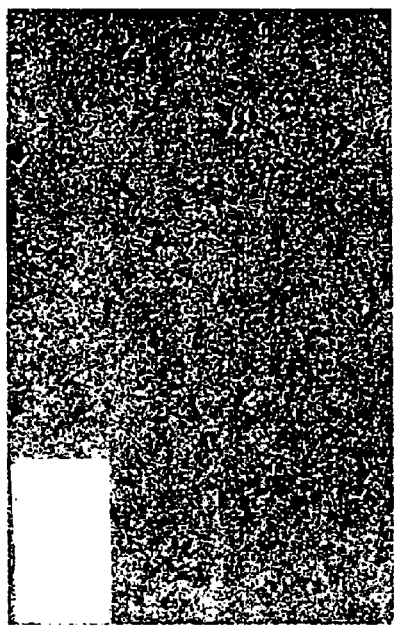
FIGS. 10A–D are photographs of neuronal tissue showing increased TUNEL-positive labeling of neuronal nuclei in the cerebral cortex following AD7c-NTP gene transfer (FIGS. 10A, C; brown precipitates).
Figure 10D:
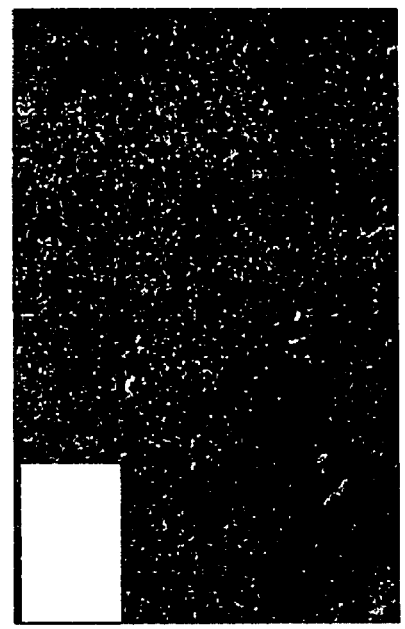
Figure 10A:
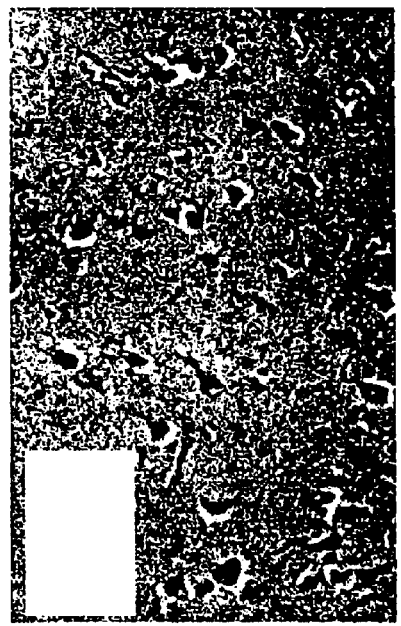
Figure 10C:
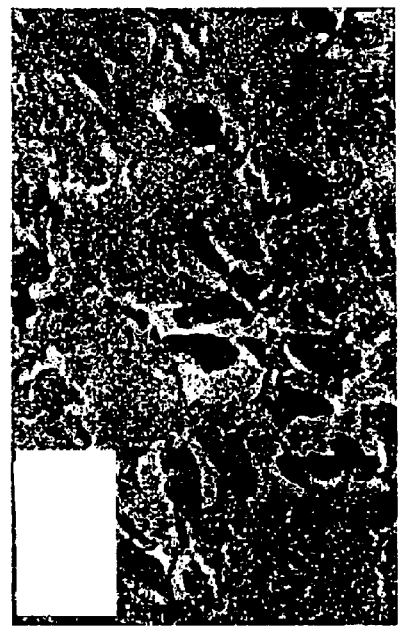
Figure 11A:
FIGS. 11A–C are photographs of neuronal tissue showing increased levels of the p53 pro-apoptosis gene expression in rat brains following AD7c-NTP gene transfer (FIGS. 11A, B).
Figure 11B:
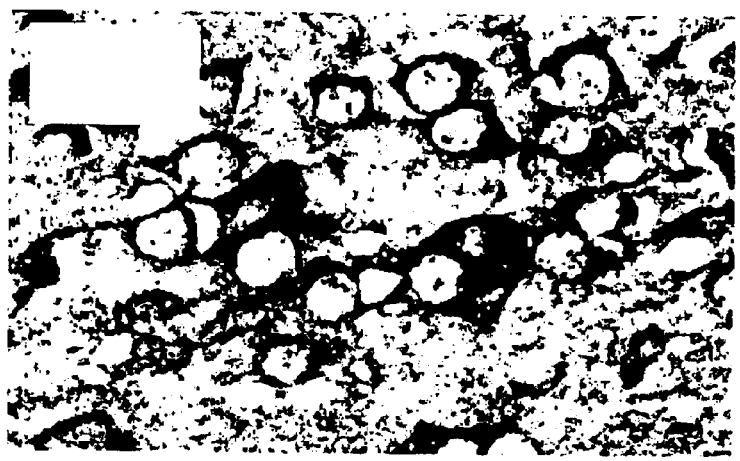
Figure 11C:
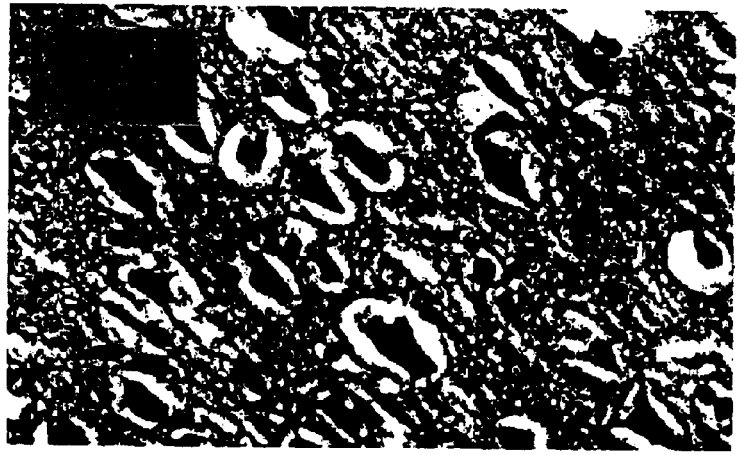
Figure 12A:
FIGS. 12A–C are photographs of neuronal tissue showing increased levels of Bax pro-apoptosis gene expression in rat brains following AD7c-NTP gene transfer (FIGS. 12A,B).
Figure 12B:
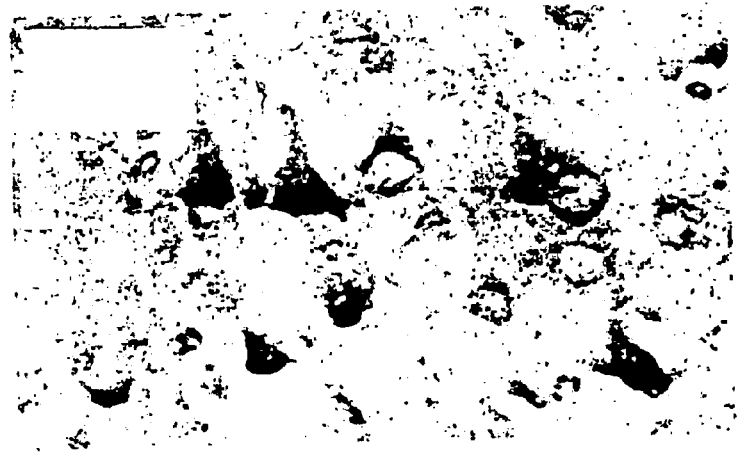
Figure 12C:

Western blot analysis was used to demonstrate increased expression of AD7c-NTP following in vivo gene transfer. Control brains were inoculated with recombinant plasmid DNA expressing the luciferase gene (pLuciferase). Brains were harvested 1, 2, 7, or 14 days after gene transfer. The cerebral hemispheres were hemisected and homogenized, and aliquots containing 100 μg of protein were used for the Western blot analysis. The autoradiograph shown in FIG. 8A depicts expression of the ~41 kD AD7c-NTP protein in control brains (ipsilateral to injection), and brain tissue contralateral (left side) and ipsilateral (right side) to the gene transfer. The graph shown in FIG. 8B illustrates the densitometric analysis results obtained using the Kodak Digital Science Image Station. The levels of immunoreactivity are expressed in arbitrary luminescence units.

Western blot analysis detected consistently low levels of the expected ~41 kD NTP protein in pLuciferase or pLacZ transfected brains. In contrast, brains that were transfected with pAD7c-NTP exhibited increased levels of AD7c-NTP expression within 24 hours of inoculation (FIGS. 8A–B). Between 1 and 14 days after gene transfer, the levels of AD7c-NTP protein increased. The highest levels of AD7c-NTP expression were observed in the right cerebral hemisphere, ipsilateral to the inoculation. In the left hemisphere, the levels of AD7c-NTP expression were initially much lower than on the right, but still higher than control. Over time, the levels of AD7c-NTP expression also increased in the left cerebral hemisphere, contralateral to the side of inoculation, and although the peak levels observed after 14 days were below those measured on the right side (FIG. 8A). These results were reproduced in three separate experiments using at least 6 animals per group.

Effects of pAD7c-NTP Gene Transfer on Neuronal Viability in the Cerebral Cortex

Brains were harvested 1 week after gene transfer. Histological sections of brains inoculated with pLacZ or pAD7c-NTP were stained. Hematoxylin and eosin-stained paraffin sections of the entire brain were examined under code to determine the effects of AD7c-NTP over-expression in vivo. The inoculation sites were excluded from the analysis. Brains harvested 24 to 96 hours after pAD7c-NTP, pLacZ, or pLuc gene transfer had similar appearances and could not be distinguished. However, after one week, the brains inoculated with pAD7c-NTP exhibited increased neuronal cell death manifested by disappearance of cell bodies and the appearance of ghost cells (FIGS. 9A–D). Neuronal cell loss was detectable in brains harvested up to 4 weeks after pAD7c-NTP gene transfer. Control brains harvested over the same interval consistently exhibited normal neuronal morphology similar to un-inoculated specimens. These data indicate that rodent brains inoculated with pAD7c-NTP exhibited neuronal loss with scattered pale, irregular neurons that lacked nuclei (ghost cells), as well as evidence of a cluster of dying neurons. These features mimic the features in human Alzheimer's Disease.

Effects of pAD7c-NTP Gene Transfer on Neuronal Apoptosis and Pro-apoptotic Gene Expression Over-expression of AD7c-NTP resulted in increased neuronal apoptosis and apoptosis proneness, manifested by higher densities of TUNEL+ nuclei, and increased immunoreactivity corresponding to the p53 and Bax pro-apoptosis gene products (FIGS. 10A–D, FIGS. 11A–C, and FIGS. 12A–C).

Increased TUNEL-positive labeling of neuronal nuclei was observed in the cerebral cortex following AD7c-NTP gene transfer compared to the control (rat brains inoculated with the Luciferase control gene). Tissue sections examined 1 week after gene transfer into the right lateral ventricle and cerebral hemisphere. TUNEL labeling of nuclei reflects increased genomic DNA nicking and fragmentation as occur prior to apoptosis.

Increased levels of the p53 pro-apoptosis gene expression were seen in rat brains following AD7c-NTP gene transfer compared to a negative control rat brain inoculated with the Luciferase gene. Tissue sections examined 1 week after gene transfer into the right lateral ventricle and cerebral hemisphere. An increase in AD7c-NTP-induced p53 expression was also detected in cortical neurons compared with control cerebral cortical neurons.

Increased levels of Bax pro-apoptosis gene expression in rat brains was detected following AD7c-NTP gene transfer compared to negative control rat brains inoculated with the Luciferase gene. Tissue sections examined 1 week after gene transfer into the right lateral ventricle and cerebral hemisphere. An increase in AD7c-NTP-induced Bax expression was observed in cortical neurons compared with control cerebral cortical neurons.

The damaged cells were identified as neuronal based upon their pyramidal shape, large size (>8 microns diameter), distribution within the cerebral cortex, and positive labeling with anti-Hu in adjacent sections. The increased apoptosis (TUNEL+) and pro-apoptotic gene (p53, Bax) expression were detected one week after pAD7c-NTP inoculation. The levels and distribution of cellular labeling were initially higher ipsilateral to the inoculations, but after two weeks, the two hemispheres were somewhat similar in these regards, corresponding with the more symmetrical distribution of AD7c-NTP expression, as demonstrated by Western blot analysis.

Effects of pAD7c-NTP Gene Transfer on AD7c-NTP, Phospho-tau and Synaptophysin Immunoreactivity in the Cerebral Cortex Immunohistochemical staining performed with a monoclonal antibody, which binds to AD7c-NTP (e.g., the N2U6) revealed low levels of diffuse neuropil labeling in the pLacZ-or or pLuciferase-inoculated control brains, and increased AD7c-NTP immunoreactivity in cortical neurons and neuritic plaque-like structures in brains inoculated with pAD7c-NTP Increased neuronal thread protein (NTP) expression in rat brains following AD7c-NTP gene transfer compared to the level detected in a negative control rat brain inoculated with the Luciferase gene. Tissue sections were examined 2 weeks after gene transfer into the right lateral ventricle and cerebral hemisphere. Increased NTP immunoreactivity was found in cortical and hippocampal neurons and neuritic plaques in brains that over-express AD7c-NTP compared with negative control cortical neurons (FIGS. 13A–F)

Figure 13A:
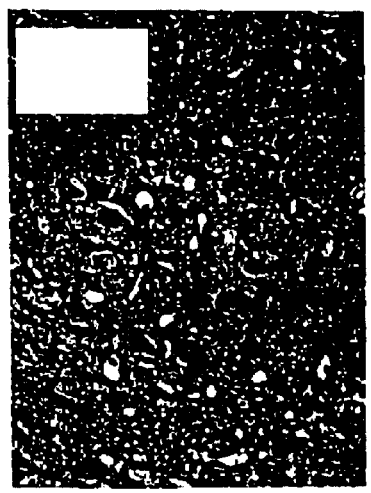
FIGS. 13A–F are photographs of neuronal tissue showing increased neuronal thread protein (NTP) expression in rat brains following AD7c-NTP gene transfer.
Figure 13B:
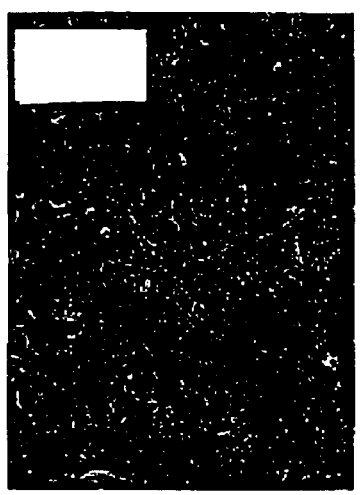
Figure 13C:
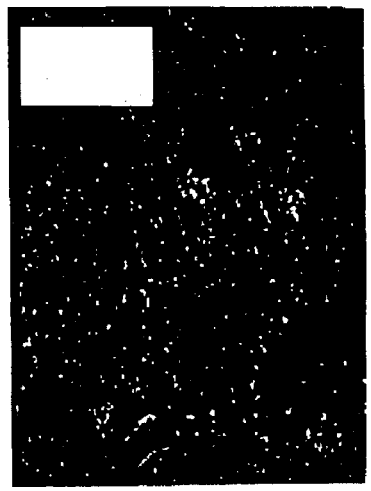
Figure 13D:
Figure 13E:
Figure 13F:
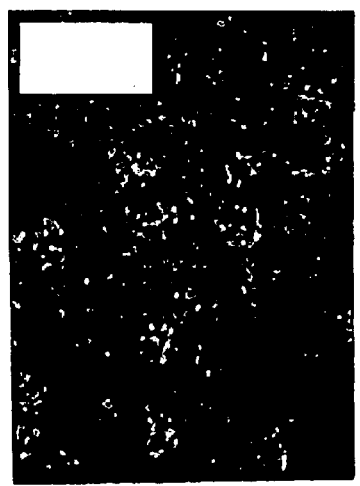

In scattered neurons the AD7c-NTP immunoreactivity was localized asymmetrically imparting an inclusion-like appearance (FIG. 13D)

Correlation with other Markers of Alzheimer's Disease Associated Neurodegeneration To determine the effects of AD7c-NTP over-expression on other genes and proteins previously linked to neurodegeneration, adjacent sections immunostained with antibodies to phospho-tau, amyloid precursor protein, amyloid-b peptide, and synaptophysin.

Aberrant synaptophysin expression was detected in rat brains after AD7c-NTP gene transfer compared to similar regions of rat brains inoculated with the Luciferase control gene. Tissue sections were examined 1 week after gene transfer into the right lateral ventricle and cerebral hemisphere.

All brains inoculated with pAD7c-NTP exhibited increased levels of phospho-tau localized in neurons and neuritic plaque-like structures (FIGS. 14A–D). Increased phospho-tau immunoreactivity was often abnormally localized in neuronal nuclei in the cerebral cortex of brains expressing exogenous AD7c-NTP. The phospho-tau-immunoreactive plaques were distributed in the cerebral cortex and in deep gray matter structures. Control brains exhibited only diffuse low levels of phospho-tau immunoreactivity and no evidence of neuritic plaque formation.

One of the most striking findings was the increased APP and amyloid-β immunoreactivity that occurred 1 to 2 weeks after AD7c-NTP gene transfer (FIGS. 15A–E and FIGS. 16A–F).

Increased phospho-Tau (pTau) expression in rat brains after AD7c-NTP gene transfer compared to rat cerebral tissue inoculated with the Luciferase control gene. Tissue sections were examined 2 weeks after gene transfer into the right lateral ventricle and cerebral hemisphere. Abnormally increased pTau immunoreactivity in neuronal nuclei from AD7c-NTP brains compared to a similar region of a control brain in which labeling was absent. The brains inoculated with the AD7c-NTP cDNA also exhibited pTau-immunoreactive neuritic plaques.

Figure 15A:
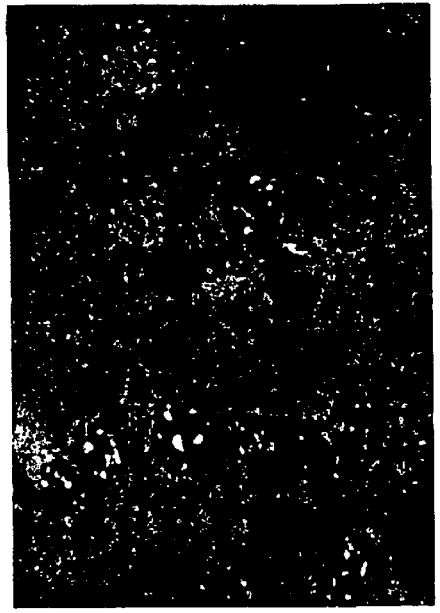
FIGS. 15A–E are photographs of neuronal tissue showing increased phospho-Tau (pTau) expression in rat brains after AD7c-NTP gene transfer (FIGS. 15A, C–E).
Figure 15B:
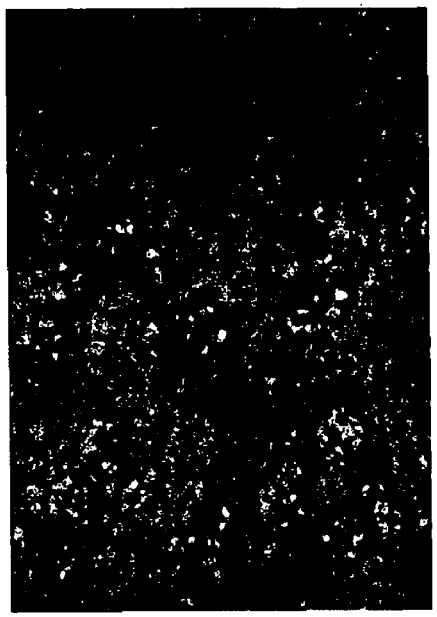
Figure 15C:
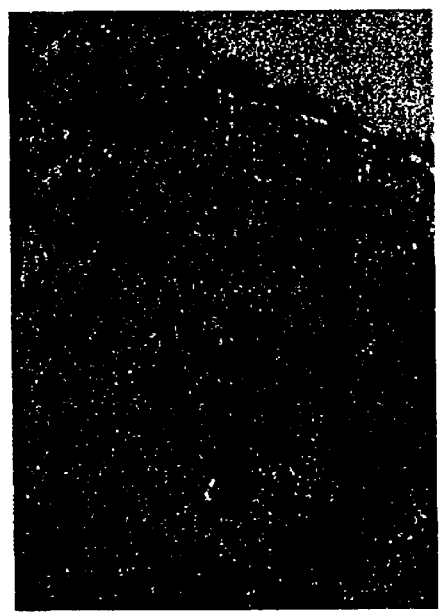
Figure 15D:
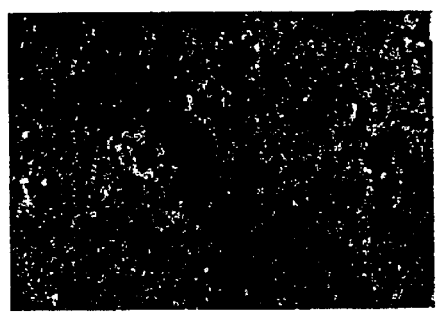
Figure 15E:
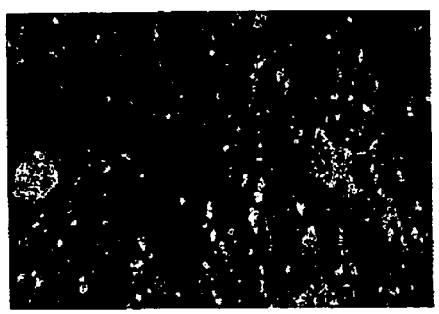

Increased amyloid precursor protein (APP) expression was observed in rat brains following AD7c-NTP gene transfer compared to a negative control rat brain inoculated with the Luciferase gene. Tissue sections were examined 2 weeks after gene transfer into the right lateral ventricle and cerebral hemisphere. An increase in APP immunoreactivity was detected in cortical neurons compared with control cerebral cortex. Intense APP immunoreactivity was seen in hippocampal neurons and in dense core or neuritic plaque-like structures Robust APP immunoreactivity was detected in cortical neurons (FIGS. 15A,B), hippocampal neurons, some of which were degenerating (FIG. 15C), and in plaque-like structures that had the appearance of dense-cores (FIG. 15C) or neuritic structures (FIGS. 15D, E). The plaque-like lesions were scattered among APP-positive cortical neurons, but some appeared to be associated with small vessels. Control brains exhibited APP immunoreactivity in the choroid plexus and initially (24–72 hours after inoculation) adjacent to the injections site, but not 1 or 2 weeks post gene transfer (FIG. 15E).

Figure 16A:
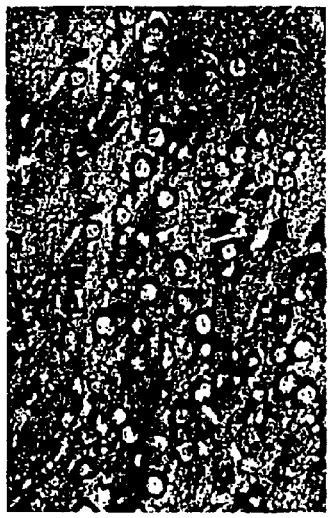
FIGS. 16A–F are photographs of neuronal tissue showing increased amyloid precursor protein (APP) expression in rat brains following AD7c-NTP gene transfer (FIGS. 16A–E).
Figure 16B:
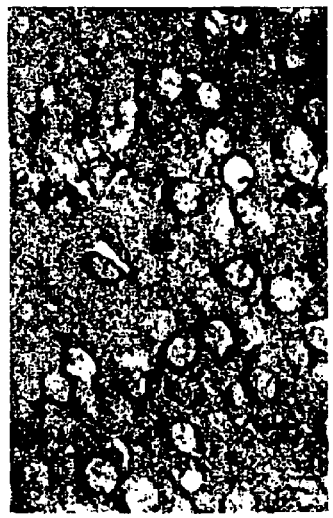
Figure 16C:
Figure 16D:
Figure 16E:
Figure 16F:
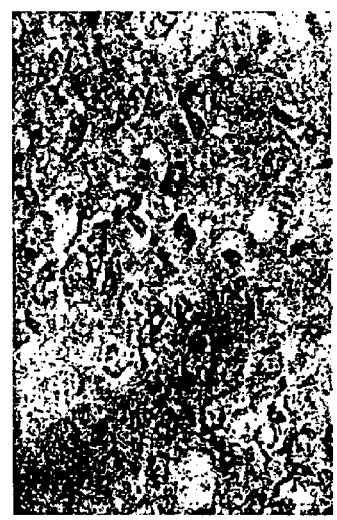
Figure 17A:
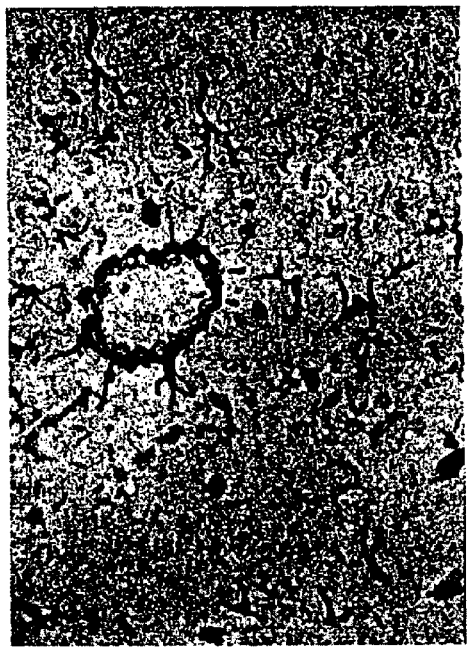
FIGS. 17A–D are photographs of neuronal tissue showing increased amyloid-beta expression in rat brains after AD7c-NTP gene transfer (FIGS. 17A, C).
Figure 17B:
Figure 17C:
Figure 17D:
Figure 18A:
FIGS. 18A–F are photographs of neuronal tissue showing increased nitric oxide synthase 3 (NOS-3) expression in rat brains following AD7c-NTP gene transfer (FIGS. 18A–D).
Figure 18B:
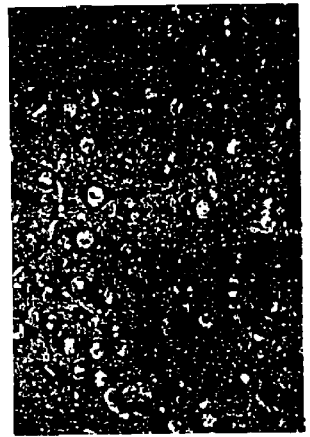
Figure 18C:
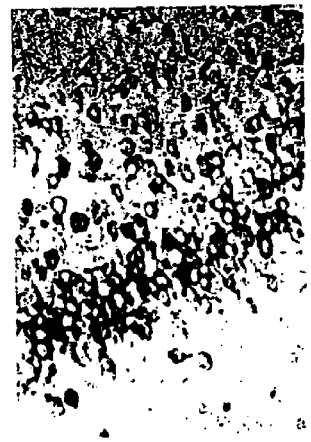
Figure 18D:
Figure 18E:
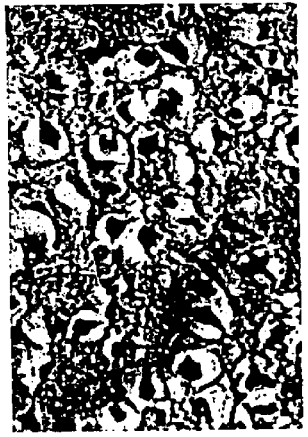
Figure 18F:
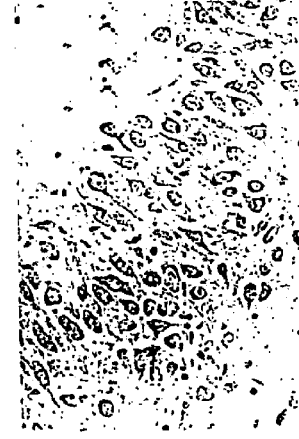

Brains inoculated with pAD7c-NTP also exhibited increased amyloid-b immunoreactivity associated with the microvasculature and medium size intraparenchymal thin-walled vessels (FIG. 16A). In addition, scattered dense-core amyloid-β-type plaques were observed in the cerebral cortex and deep gray matter structures (FIG. 16C). Neuritic plaques similar to those detected with antibodies to AD7c-NTP, phospho-tau, or APP were not observed in sections immunostained with antibodies to amyloid-β. Control brains inoculated with pLacZ or pLuc did not exhibit increased amyloid-b immunoreactivity (FIGS. 16B,D).

One of the abnormalities associated with Alzheimer's Disease associated neurodegeneration is synaptic disconnection with pruning of cortical dendritic processes. These abnormalities have been revealed with antibodies to synaptophysin. In brains inoculated with pAD7c-NTP, the patterns and distribution of synaptophysin immunoreactivity were strikingly altered. Instead of the diffuse labeling of neuropil fibers observed in pLacZ or pLuc inoculated control brains, over-expression of AD7c-NTP resulted in prominent perikaryal labeling and only low levels of synaptophysin immunoreactivity distributed diffusely throughout the neuropil (FIGS. 17-A–D). Dense cores of amyloid beta resembling senile plaques that occur in human brains with Alzheimer's Disease were found in the AD7c-NTP brains.

Correlation with Nitric Oxide Synthase-3 Expression

NOS-3 expression in increased in cortical neurons in brains with Alzheimer's Disease beginning early in the course of neurodegeneration. Abnormally increased levels of NOS-3 immunoreactivity in brains with Alzheimer's Disease as well as other forms of neurodegeneration are associated with apoptosis and apoptosis proneness mediated in part by increased production of peroxynitrite. Since abnormalities in AD7c-NTP and NOS-3 expression begin at approximately the same time period in Down syndrome, which represents a natural human model of Alzheimer's Disease associated neurodegeneration, studies were undertaken to determine if NOS-3 expression was linked and downstream of AD7c-NTP. Immunohistochemical staining studies showed sharply increased levels of NOS-3 immunoreactivity in cortical and hippocampal neurons of brains inoculated with pAD7c-NTP, compared with minimal NOS-3 expression in control brains (FIGS. 18A–F). In contrast, in vivo gene transfer studies done with pNOS-3 did not result in increased AD7c-NTP NTP expression. Inoculation with pNOS-3 did result in increased expression of APP and amyloid-b accumulation as indicating that some of the effects of AD7c-NTP over-expression are mediated by secondary induction of NOS-3 expression.

AD7c-NTP Induced Neurodegeneration Following in vivo Gene Transfer

In vitro transfection studies demonstrated that over-expression of AD7c-NTP results in neurodegeneration characterized by increased neuronal cell death mediated by apoptosis and impaired mitochondrial function, and associated increased expression of phospho-tau and the p53 pro-apoptosis gene. However, long term expression of this gene or other genes has not been possible until the present demonstration thereof The gene transfer system described herein provides a method for inducing prolonged in vivo gene expression in non-skeletal muscle tissue using a formulation, which contains a nucleic acid, a histone protein, a liposome, and an amphipathic compound. The system was used to examine the effects of AD7c-NTP over-expression in vivo. Western blot analysis revealed substantially higher levels of the expected ~41 kD AD7c-NTP protein in brains inoculated with pAD7c-NTP compared with brains inoculated with pLuc or pLacZ controls. Analysis of the time course of gene expression revealed that increased AD7c-NTP protein expression or b-galactosidase activity were detectable 24 hours after gene inoculation, but large increases in gene expression were detected only after one or two weeks. Further studies revealed sustained high-level gene expression in vivo for over 2 months, in contrast to the short-duration of gene expression (days) typically observed in transiently transfected cell lines. No other gene delivery system has accomplished the long term expression profile in non-muscular tissue. The data indicate that post-mitotic neuronal cells retain and express recombinant plasmid DNA for long intervals after transfection using the described mixture of components. These results indicate that the formulations described herein are useful for CNS gene therapy.

Histological studies demonstrated neuronal loss and increased densities of ghost neurons (faded with loss of nuclear detail) in brains that over-expressed the AD7c-NTP gene. Increased apoptosis was demonstrated using the in situ TUNEL assay, which detects fragmentation and nicking of genomic DNA. The associated increases in Bax and p53 expression in cortical neurons suggest that AD7c-NTP causes apoptosis by activating pro-apoptosis mechanisms as observed in brains with AD.

Brains inoculated with pAD7c-NTP exhibited altered synaptophysin immunoreactivity characterized by a shift from diffuse neuropil labeling to prominent perikaryal and virtually absent neuropil labeling. This altered distribution of synaptophysin immunoreactivity is consistent with either neurite retraction or failure to transport synaptic proteins, and is similar to the synaptic loss/disconnection associated with Alzheimer's Disease associated neurodegeneration.

In addition to increased neuronal cell death mediated by apoptosis and pro-apoptosis gene activation, brains inoculated with pAD7c-NTP exhibited increased expression of phospho-tau, APP, and amyloid-b. The increased levels of phospho-tau and APP immunoreactivity were localized in neurons and neuritic-like plaques. The findings with respect to phospho-tau are consistent with previous studies, which correlated over-expression of AD7c-NTP with phospho-tau-accumulation in Alzheimer's Disease brains and CSF. The findings indicate that increased AD7c-NTP expression precedes phospho-tau accumulation in the course of Alzheimer's Disease associated neurodegeneration, consistent previous observations in brain tissue taken from patients with Alzheimer's Disease.

The findings of increased levels of both APP and amyloid-b immunoreactivity in brains inoculated with pAD7c-NTP were unexpected. The distributions of increased APP and amyloid-b immunoreactivity were distinct in that the APP was localized in neuronal perikarya and neuritic plaques, whereas the amyloid-b deposits were mainly distributed in small vessels and dense core-type plaques, similar to the findings in brains with AD. The implication is that abnormal processing of APP to generate amyloid-b may occur in selected brain regions and primarily in relation to the microvasculature rather than every location or cell type that exhibits increased APP expression.

Over-expression of AD7c-NTP resulted in increased levels of NOS-3 expression in numerous cortical neurons, as well as in the microvasculature. The distribution of aberrantly increased NOS-3 expression paralleled that of APP. Additional studies in which brains were inoculated with pNOS-3 were done to determine if the increased expression NOS-3 represented a secondary response to AD7c-NTP over-expression. The findings were that NOS-3 over-expression resulted in increased levels of NOS-3, APP, and amyloid-b immunoreactivity, as well as increased p53 and Bax pro-apoptosis gene expression, but had no effect on the levels of AD7c-NTP. These data indicate that over-expression of AD7c-NTP in the brain leads to increased levels of NOS-3, which in turn activates pro-apoptosis mechanisms and promotes high levels of APP expression and amyloid-b accumulation. This scenario accounts for the co-occurrence of abnormal NOS-3 and AD7c-NTP expression with progression of Alzheimer's Disease associated neurodegeneration in brains with Down's syndrome. NOS's and APP mediate their effects in part by signaling through G proteins, establishing a link between amyloid- and NOS-mediated neuronal degeneration.

With aging, the brain expresses reduced levels of cGMP due to increased degradation by phosphodiesterases. Reduced NO signaling through cGMP-dependent pathways results in increased oxidative stress and heightened sensitivity to amyloid-b-toxicity. With regard to AD7c-NTP over-expression, the high levels of NOS-3 and APP likely overwhelm G-protein signaling mechanisms, leading to increased oxidative stress and activation of pro-apoptosis signaling pathways. In the human brain, another important factor contributing to oxidative stress-mediated the activation of the AD7c-NTP-NOS-3-APP-apoptosis cascade with aging and neurodegeneration is progressive impairment of mitochondrial function due to cumulative mitochondrial DNA damage. Moreover, oxidative stress, free radical injury, and excitotoxicity in the brain have been correlated with a number of AD-associated molecular abnormalities including amyloid-b deposition, increased phospho-tau expression, and NOS activation. Using the in vivo animal model of neurodegeneration described herein, the data indicate the following scheme in the progression of Alzheimer's Disease (e.g., sporadic Alzheimer's Disease):

High levels of AD7c-NTP→increased NOS-3 expression→increased APP →overwhelming of cGMP pathway→NO-mediated oxidative stress→phospho-Tau accumulation and activation of pro-apoptosis mechanisms.

The scheme indicates that there are multiple points of interfering with the adverse effects of AD7c-NTP overexpression to at least partially rescue of Alzheimer's Disease associated neurodegeneration.

Other embodiments are within the following claims.

What is claimed is:

1. A non-transgenic model for Alzheimer's Disease, comprising a non-human mammal, wherein the neuronal cells of said mammal comprise a composition comprising a heterologous AD7c-NTP nucleic acid, histone, and amphipathic compound, and wherein expression of said heterologous AD7C-NTP nucleic acid is detected in neuronal tissue of said mammal at least 4 weeks after contacting said mammal with said composition and wherein said expression results in Alzheimer's Disease-associated neuronal cell death.

2. The model of claim 1, wherein said mammal is a rodent.

3. The model of claim 1, wherein said mammal is a non-human primate.

4. The model of claim 1, wherein said neuronal cell is selected from the group consisting of a cortical neuronal cell, a hippocampal neuronal cell, a cerebellar neuronal cell, and a glial cell.

5. A method of identifying a compound which inhibits Alzheimer's Disease-associated neuronal cell death, comprising contacting the model of claim 1 expressing a heterologous AD7c-NTP nucleic acid in a neuronal tissue of said animal with a candidate compound and measuring neuronal cell viability, wherein an increase in cell viability in the presence of the compound compared to in its absence indicates that said compound inhibits Alzheimer's Disease-associated neuronal cell death.

6. A method of identifying a compound which inhibits amyloid precursor protein (APP) expression comprising contacting the model of claim 1 with a candidate compound and detecting (APP) expression in neuronal tissue of said mammal, wherein a decrease in APP expression in the presence of the compound compared to in its absence indicates that said compound inhibits expression of APP.

7. A method of identifying a compound which inhibits amyloid plaque formation, comprising contacting the model of claim 1 with a candidate compound and detecting amyloid plaques in neuronal tissue, wherein a decrease in the amount of said plaques in the presence of the compound compared to in its absence indicates that said compound inhibits amyloid plaque formation.

8. The model of claim 1 wherein said AD7c-NTP nucleic acid comprises the nucleotide sequence of SEQ ID NO:1.

9. The model of claim 1, wherein said wherein expression of said heterologous AD7c-NTP nucleic acid is detected in neuronal tissue of said mammal at least 2 months after contacting said mammal with said composition.

10. The method of claim 1, wherein said histone is selected from the group consisting of H1, H2A, H2B, H3, and H4.

11. The method of claim 1, wherein the amphipathic compound is a non-natural polyamine having a hydrophobic moiety, said polyamine being selected from the group consisting of a C6–C24 alkane, C6–C24 alkane, sterol, steroid, lipid, fatty acid, and hydrophobic hormone.

12. The method of claim 1, wherein said nucleic acid is an AD7c-NTP antisense molecule or a nitric oxide synthase III antisense molecule.

* * * * *